(12) United States Patent
Nikolaidis et al.

(10) Patent No.: US 9,999,777 B2
(45) Date of Patent: Jun. 19, 2018

(54) CERMET FEEDTHROUGH IN CERAMIC MULTILAYER BODY

(71) Applicant: Heraeus Deutschland GmbH & Co. KG, Hanau (DE)

(72) Inventors: Ilias Nikolaidis, Hanau (DE); Frederik Roth, Bruchköbel (DE); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days. days.

(21) Appl. No.: 15/679,993

(22) Filed: Aug. 17, 2017

(65) Prior Publication Data

US 2018/0050210 A1 Feb. 22, 2018

(30) Foreign Application Priority Data

Aug. 17, 2016 (EP) .................. 16184555.7

(51) Int. Cl.
| | |
|---|---|
| *H01B 5/00* | (2006.01) |
| *H05K 1/11* | (2006.01) |
| *A61N 1/375* | (2006.01) |
| *C22C 29/00* | (2006.01) |
| *H01M 2/06* | (2006.01) |
| *H01G 4/35* | (2006.01) |
| *C22C 29/12* | (2006.01) |

(52) U.S. Cl.
CPC .......... *A61N 1/3754* (2013.01); *C22C 29/005* (2013.01); *C22C 29/12* (2013.01); *H01G 4/35* (2013.01); *H01M 2/065* (2013.01)

(58) Field of Classification Search
CPC .... A61N 1/3754; C22C 29/005; C22C 29/12; H01M 2/065; H01G 4/35
USPC .............................. 174/126.2, 262
See application file for complete search history.

(56) References Cited

U.S. PATENT DOCUMENTS

| | | | | |
|---|---|---|---|---|
| 4,488,673 A | * | 12/1984 | Hopper, Jr. .............. | B23K 1/20 228/122.1 |
| 5,738,270 A | * | 4/1998 | Malmgren ............ | A61F 2/0095 228/124.6 |
| 5,796,019 A | | 8/1998 | Lupton et al. | |
| 5,855,995 A | | 1/1999 | Haq et al. | |
| 2011/0000699 A1 | * | 1/2011 | Bealka ..................... | H01G 4/35 174/151 |
| 2011/0034965 A1 | * | 2/2011 | Troetzschel ......... | A61N 1/3754 607/37 |

(Continued)

FOREIGN PATENT DOCUMENTS

| | | |
|---|---|---|
| DE | 102009035972 | 4/2011 |
| EP | 1897588 | 3/2008 |

*Primary Examiner* — Sherman Ng
(74) *Attorney, Agent, or Firm* — Dicke, Billig & Czaja, PLLC

(57) ABSTRACT

One aspect generally relates to a composite, having a layer sequence. The layer sequence includes as layers a first layer, including a first ceramic, and first layer surface, a second layer, including a second ceramic, superimposing the first layer surface. The layer sequence includes a hole, connecting through each layer of the layer sequence; and a cermet. The cermet includes a first part and a second part. The first part is included by the hole. The second part is included between the first layer and the second layer. The cermet is in one piece.

16 Claims, 15 Drawing Sheets

(56) References Cited

U.S. PATENT DOCUMENTS

| | | | |
|---|---|---|---|
| 2012/0193117 A1* | 8/2012 | Specht | A61N 1/3754 |
| | | | 174/50.53 |
| 2012/0193119 A1 | 8/2012 | Kempf et al. | |
| 2012/0197326 A1* | 8/2012 | Pavlovic | H01R 43/20 |
| | | | 607/5 |
| 2012/0197327 A1* | 8/2012 | Specht | H01R 13/5224 |
| | | | 607/5 |
| 2012/0200011 A1* | 8/2012 | Pavlovic | A61N 1/3754 |
| | | | 264/614 |
| 2013/0338750 A1 | 12/2013 | Eck et al. | |
| 2015/0165219 A1 | 6/2015 | Markham et al. | |
| 2016/0153929 A1 | 6/2016 | Rottmann et al. | |

* cited by examiner

1000

CERMET FEEDTHROUGH IN CERAMIC MULTILAYER BODY

CROSS-REFERENCE TO RELATED APPLICATIONS

This Utility Patent Application claims priority to European Patent Application No. EP 16184555.7, filed on Aug. 17, 2016, which is incorporated herein by reference.

BACKGROUND

One embodiment relates to a composite comprising a ceramic multilayer body, comprising a cermet feedthrough; to a process for manufacturing a composite, comprising a cermet feedthrough; to a composite obtainable by said process; to a device comprising a composite according to one embodiment; and to a use of a plurality of ceramic green sheets and a composition to produce a composite according to one embodiment.

The prior art knows numerous implantable electrical medical devices, for example pacemakers and defibrillators. Pacemakers known in the prior art include a bladder pacemaker, a breath pacemaker, an intestinal pacemaker, a diaphragm pacemaker, a cerebral pacemaker and a cardiac pacemaker. Such devices commonly include a housing enclosing electronics. An electrical source of energy, for example, a battery, may be included by the housing as well or it may be included by a further housing and be connected to the electronics via electrical connectors. The housing which is to be implanted into a human or animal body must hermetically seal the electronics from the surrounding body, that is, it must be leak tight for body fluids and gases. Commonly an object of an implantable electrical medical device involves electrically stimulating tissue, that is, muscles or brain cells, via electrodes or measuring electrical signals of the body via antennae, or both. Therefore, the implantable electrical medical device has to include an electrical feedthrough which electrically connects the inside of the housing to the outside. Such a feedthrough has to be designed to maintain the housing hermetically tight and thus the device implantable. Therefore, an electrical feedthrough for implantable medical devices commonly known in the prior art includes an electrically conductive feedthrough element, here a metal feedthrough wire, which is enclosed by a ceramic ring. Therein, the feedthrough wire is soldered to the ceramic ring via a gold solder. The ceramic ring in turn is soldered into a metal flange, which can be welded to a metal housing. Said feedthrough assembly of the prior art includes several intermaterial connections which may be prone to breaking or leaking. In addition, establishing such intermaterial connections is costly or makes a production process more complicated or lengthy. An improved feedthrough is disclosed in EP 1 897 588 B1. Therein, the metal feedthrough wire is connected to a surrounding ceramic body by means of sintering. This way the number of intermaterial connections and the amount of gold solder used are reduced. The connection between the electrically conductive feedthrough element and the ceramic body could be improved by means of the disclosure of DE 10 2009 035 972 A1. Therein, a feedthrough element made of a cermet is used instead of a metal feedthrough element.

In order to tailor a ceramic body of a desired thickness or quality or both the ceramic body can include multiple ceramic layers. The feedthrough element then electrically connects through the ceramic layers of the ceramic body. Such a multilayer feedthrough may be prepared by stacking and laminating ceramic green sheet tapes, providing holes which connect through the laminate of the green sheet tapes, filling a cermet into the holes and sintering the green sheet tapes and the cermet together by firing at a peak temperature above 1400° C. Therein, the material of the ceramic green sheet tapes and the cermet have to be chosen to have very similar characteristics of their coefficients of thermal expansion (CTE) and sintering. Any mismatch in CTE and/or sintering characteristics of the materials may result in a mechanical stress between the parts upon firing. Said stress may lead to a delamination of the ceramic layers in the surroundings of the cermet or even to a structural damage of the ceramic body.

Therefore, the cermet feedthroughs in ceramic multilayer bodies known in the prior art include at least the following disadvantages. Only small mismatches of CTE or sintering characteristics or both of ceramic materials and cermet materials used for cermet feedthroughs in ceramic multilayer bodies of the prior art are tolerable. The choice of ceramic or cermet or both materials which can be applied for cermet feedthroughs in ceramic multilayer bodies of the prior art are undesirably limited. The choice of combinations of ceramic and cermet materials which can be applied for cermet feedthroughs in ceramic multilayer bodies of the prior art are undesirably limited. Upon producing cermet feedthroughs in ceramic multilayer bodies of the prior art an undesirably high fraction of defect or substandard or both feedthroughs are obtained. An undesirably high effort has to be put into the sintering step of producing cermet feedthroughs in ceramic multilayer bodies of the prior art. Producing cermet feedthroughs in ceramic multilayer bodies of the prior art is undesirably complicated. Producing cermet feedthroughs in ceramic multilayer bodies of the prior art is undesirably expensive.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1b is a detailed scheme of the cermet element of FIG. 1a;

FIG. 3b is a detailed scheme of the further cermet element of FIG. 3a;

FIG. 12b is a another schematic cross sectional side view of the composite according to the embodiment of FIG. 12a;

DETAILED DESCRIPTION

Figure 1A:
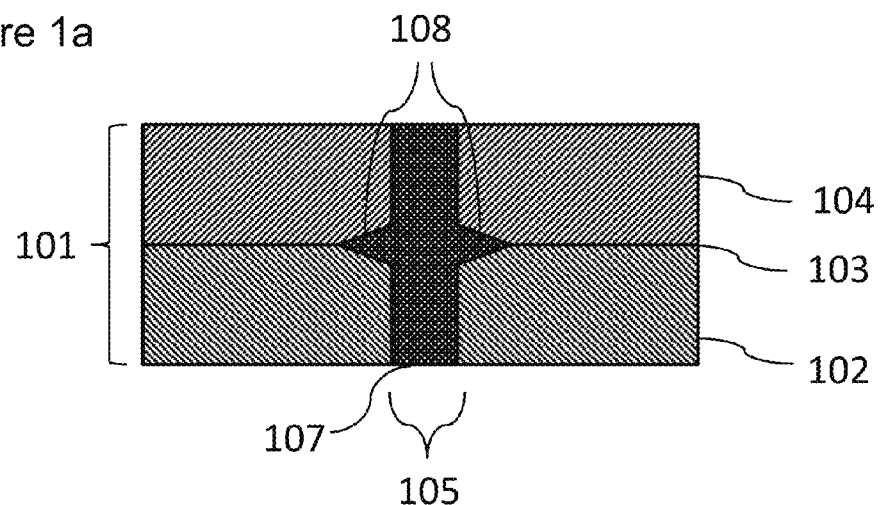
FIG. 1a is a schematic cross sectional side view of composite according to one embodiment.

In the following Detailed Description, reference is made to the accompanying drawings, which form a part hereof, and in which is shown by way of illustration specific embodiments that may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments is defined by the appended claims.

It is to be understood that the features of the various exemplary embodiments described herein may be combined with each other, unless specifically noted otherwise.

Generally, one embodiment at least partly overcome a disadvantage arising from the prior art. One embodiment provides a cermet feedthrough in a ceramic multilayer body to which a wider range of materials or a wider range of material combinations or both is applicable. One embodiment provides a cermet feedthrough in a ceramic multilayer body, wherein delamination of a ceramic multilayer body upon sintering is reduced or prevented or both. One embodiment provides a cermet feedthrough in a ceramic multilayer body, wherein a structural damage of the ceramic multilayer body upon sintering is reduced or prevented or both. One embodiment provides a cermet feedthrough in a ceramic multilayer body, wherein the feedthrough is more durable, for example with respect to thermal stress or mechanical stress or both. One embodiment provides a production method for a cermet feedthrough in a ceramic multilayer body which illustrates at least one of the above advantages. One embodiment provides a method of producing a cermet feedthrough in a ceramic multilayer body, wherein the method results in producing less defect or substandard or both feedthroughs. One embodiment provides a means of producing a cermet feedthrough in a ceramic multilayer body, wherein producing is less expensive or less compli- cated or both. One embodiment provides a medical implantable electrical device comprising a cermet feedthrough in a ceramic multilayer body, wherein the feedthrough illustrates at least one of the above advantages. One embodiment provides a pacemaker or a biomonitor or both comprising a cermet feedthrough in a ceramic multilayer body, wherein the feedthrough illustrates at least one of the above advantages. One embodiment provides a medical implantable electrical device which is characterised by a longer durability period in a body. One embodiment provides a medical implantable electrical device which is less prone to defects when being used in a body. One embodiment provides a medical implantable electrical device which works more reliable when implanted in a body. One embodiment provides a medical implantable electrical device which is less complicated or less expensive or both to produce. One embodiment provides a pacemaker or a biomonitor or both which is characterised by at least one of the above advantages of a medical implantable electrical device. One embodiment provides a header block for a medical implantable electrical device which includes less parts. One embodiment provides a header block for a medical implantable electrical device which is less complicated or less costly or both to produce. One embodiment provides a header block for a medical implantable electrical device which has a more simple design. One embodiment provides a header block for a medical implantable electrical device which includes less brazings. One embodiment provides a header block for a medical implantable electrical device which allows a higher number of lead connections.

A contribution to the solution of at least one of the above is made by a composite, comprising a layer sequence;
  wherein the layer sequence
  a) includes as layers
    i) a first layer, comprising
      A. a first ceramic, and
      B. a first layer surface,
    ii) a second layer,
      A. comprising a second ceramic,
      B. superimposing the first layer surface;
  b) includes
    i) a hole, connecting through each layer of the layer sequence;
    ii) a cermet element;
  wherein the cermet element includes a first part and a second part;
  wherein the first part is included by the hole;
  wherein the second part is included between the first layer and the second layer;
  wherein the cermet element is in one piece. In one embodiment a ratio of a length of the second part to a thickness of the second part at its widest portion is in the range of from 1 to 70, in one embodiment from 1 to 60, in one embodiment from 1 to 50, in one embodiment from 1 to 45, in one embodiment from 1 to 40, in one embodiment from 1 to 35, in one embodiment from 1 to 30, in one embodiment from 1 to 25, in one embodiment from 1 to 20, in one embodiment from 1 to 15, in one embodiment from 1 to 10, in one embodiment from 1 to 5.

In one embodiment, the layer sequence further includes n layers;
  wherein each $i^{th}$ layer includes an $i^{th}$ layer surface and an $i^{th}$ ceramic;
  wherein each $i^{th}$ layer superimposes the $(i-1)^{st}$ layer surface;

wherein the cermet element further includes n parts;
wherein each $i^{th}$ part is included between the $i^{th}$ layer and the $(i-1)^{st}$ layer;
wherein n is an integer, being at least 1;
wherein i is an index which can be any integer selected from the range from 2 to (n+2). In one embodiment n is at least 2, in one embodiment at least 3, in one embodiment at least 4, in one embodiment at least 5.

In another embodiment, the layer sequence includes
a) one or more further holes, each further hole connecting through each layer of the layer sequence;
b) one or more further cermet elements;
wherein each further cermet element includes a further first part and a further second part;
wherein each further first part is included by one of the further holes;
wherein each further second part is included between the first layer and the second layer;
wherein each further cermet element is in one piece. In one embodiment a ratio of a length of the further second part to a thickness of the further second part at its widest portion is in the range of from 1 to 70, in one embodiment from 1 to 60, in one embodiment from 1 to 50, in one embodiment from 1 to 45, in one embodiment from 1 to 40, in one embodiment from 1 to 35, in one embodiment from 1 to 30, in one embodiment from 1 to 25, in one embodiment from 1 to 20, in one embodiment from 1 to 15, in one embodiment from 1 to 10, in one embodiment from 1 to 5.

In another embodiment, the layer sequence includes
a) one or more further holes, each further hole connecting through each layer of the layer sequence;
b) one or more further cermet elements;
wherein each further cermet element includes (n+2) further parts;
wherein each further first part is included by one of the further holes;
wherein each further $i^{th}$ part is included between the $i^{th}$ layer and the $(i-1)^{st}$ layer;
wherein each further cermet element is in one piece. In one embodiment for each further $i^{th}$ part a ratio of a length of said further $i^{th}$ part to a thickness of said further $i^{th}$ part at its widest portion is in the range of from 1 to 70, in one embodiment from 1 to 60, in one embodiment from 1 to 50, in one embodiment from 1 to 45, in one embodiment from 1 to 40, in one embodiment from 1 to 35, in one embodiment from 1 to 30, in one embodiment from 1 to 25, in one embodiment from 1 to 20, in one embodiment from 1 to 15, in one embodiment from 1 to 10, in one embodiment from 1 to 5.

In another embodiment, the cermet element; or at least one of the further cermet elements, each further cermet element; or both includes
a) Pt in the range from 60 wt.-% to the remainder completing the sum of all components to 100 wt.-%, in one embodiment from 65 wt.-% to the remainder completing the sum of all components to 100 wt.-%, in one embodiment from 70 wt.-% to the remainder completing the sum of all components to 100 wt.-%, even in one embodiment from 80 wt.-% to the remainder completing the sum of all components to 100 wt.-%, in one embodiment from 90 wt.-% to the remainder completing the sum of all components to 100 wt.-%; and
b) $Al_2O_3$ in the range from 0.5 to 25 wt.-%, in one embodiment in the range from 0.5 to 20 wt.-%, in one embodiment in the range from 1 to 15 wt.-%, in one embodiment in the range from 1.1 to 8 wt.-%, in one embodiment in the range from 1.7 to 4.5 wt.-%;
each based on the total weight of the cermet element, or the further cermet element.

In another embodiment, the second part has a thickness at its widest portion of at least 3 μm, in one embodiment at least 4 μm, in one embodiment at least 5 μm, in one embodiment at least 7 μm.

In another embodiment, at least one of the further second parts, in one embodiment each further second part, has a thickness at its widest portion of at least 3 μm, in one embodiment at least 4 μm, in one embodiment at least 5 μm, in one embodiment at least 7 μm.

In another embodiment, at least one $i^{th}$ part, in one embodiment each $i^{th}$ part, has a thickness at its widest portion of at least 3 μm, in one embodiment at least 4 μm, in one embodiment at least 5 μm, in one embodiment at least 7 μm.

In an embodiment, at least one further $i^{th}$ part, in one embodiment each further $i^{th}$ part, has a thickness at its widest portion at least 3μm, in one embodiment at least 4 μm, in one embodiment at least 5 μm, in one embodiment at least 7 μm.

In an embodiment, the second part has a length in the range from 5 to 200 μm, in one embodiment in the range from 7 to 150 μm, in one embodiment in the range from 10 to 100 μm, in one embodiment in the range from 20 to 80 μm.

In an embodiment, at least one further second part, in one embodiment each further second part, has a length in the range from 5 to 200 μm, in one embodiment in the range from 7 to 150 μm, in one embodiment in the range from 10 to 100 μm, in one embodiment in the range from 20 to 80 μm.

In an embodiment, at least one $i^{th}$ part, in one embodiment each $i^{th}$ part, has a length in the range from 5 to 200 μm, in one embodiment in the range from 7 to 150 μm, in one embodiment in the range from 10 to 100 μm, in one embodiment in the range from 20 to 80 μm.

In an embodiment, at least one further $i^{th}$ part, in one embodiment each further $i^{th}$ part, has a length in the range from 5 to 200 μm, in one embodiment in the range from 7 to 150 μm, in one embodiment in the range from 10 to 100 μm, in one embodiment in the range from 20 to 80 μm.

In an embodiment, the first layer or the second layer or both have a thickness in the range from 75 to 600 μm, in one embodiment in the range from 80 to 550 μm, in one embodiment in the range from 100 to 500 μm, in one embodiment in the range from 200 to 400 μm.

In an embodiment, at least one $i^{th}$ layer, in one embodiment each $i^{th}$ layer, has a thickness in the range from 75 to 600 μm, in one embodiment in the range from 80 to 550 μm, in one embodiment in the range from 100 to 500 μm, in one embodiment in the range from 200 to 400 μm.

In an embodiment, the hole has a diameter in the range from 100 to 800 μm, in one embodiment in the range from 200 to 700 μm, in one embodiment in the range from 250 to 600 μm, in one embodiment in the range from 300 to 500 μm.

In an embodiment, at least one further hole, in one embodiment each further hole, has a diameter in the range from 100 to 800 μm, in one embodiment in the range from 200 to 700 μm, in one embodiment in the range from 250 to 600 μm, in one embodiment in the range from 300 to 500 μm.

In an embodiment, the composite further includes a ceramic body, wherein the ceramic body
a) includes a ceramic body layer,
  i) comprising a ceramic body layer surface,
  ii) superimposing the layer sequence such that the ceramic body layer surface covers the hole;
b) includes a blind hole, comprising a blind hole front face, a blind hole end face, and a lateral surface;
wherein the blind hole front face is an opening in a body surface of the ceramic body;
wherein the body surface is different from the ceramic body layer surface;
wherein the blind hole end face is included by the ceramic body;
wherein the hole connects to the lateral surface;
wherein the first part of the cermet element connects to the lateral surface.

The ceramic body includes a ceramic according to one embodiment. In one embodiment, a ceramic body is a ceramic block. In one embodiment, a ceramic body includes a plurality of further ceramic body layers, wherein the ceramic layer and the further ceramic layers form a further ceramic layer sequence. In one embodiment, a body surface is not opposite to the ceramic body layer surface. In one embodiment, a body surface is adjacent to the ceramic body layer surface.

In an embodiment, the ceramic body layer superimposes the layer sequence such that the ceramic body layer surface covers at least one further hole;
wherein the at least one further hole connects to the lateral surface of the blind hole;
wherein at least one further first part of at least one further cermet element connects to the lateral surface of the blind hole. In one embodiment, the hole and each further hole each connect to different positions on a circumference of the lateral surface. In one embodiment, the first part and each further first part each connect to different positions on a circumference of the lateral surface.

In an embodiment, the blind hole includes an electrically conductive element. In one embodiment, an electrically conductive element is one selected from the group consisting of a female connector, a cermet and a spring or a combination of at least two thereof. In one embodiment, an electrically conductive element consists of more than one piece. In one embodiment, an electrically conductive element consists of as many pieces as holes and further holes are connected to the lateral surface of the blind hole which includes the electrically conductive element. In one embodiment, the pieces of the electrically conductive element are electrically insulated from each other.

In an embodiment, the ceramic body includes a plurality of further blind holes, in one embodiment at least 5 further blind holes, in one embodiment at least 10 further blind holes, in one embodiment at least 20 further blind holes; wherein each further blind hole includes a further blind hole front face, a further blind hole end face, and a further lateral surface; wherein each further blind hole front face is an opening in the body surface of the ceramic body; wherein each blind hole end face is included by the ceramic body; wherein to each further lateral surface at least one different further hole is connects; wherein to each further lateral surface of each further blind hole at least one different further first part of at least one different further cermet element connects. In one embodiment, a composite is a header block.

A contribution to the solution of at least one of the above is made by a process, comprising as process steps a) providing a first ceramic green sheet, comprising a first hole and a first ceramic green sheet surface,
wherein the first hole has a first hole volume;
b) providing a plurality of portions of a first cermet precursor composition,
wherein the plurality of portions of the first cermet precursor composition has a total first cermet precursor composition volume, wherein the total first cermet precursor composition volume is higher than the first hole volume;
c) filling the plurality of portions of the first cermet precursor composition into the first hole in subsequent fill-in steps portion by portion,
wherein after each fill-in step a filled in portion of the first cermet precursor composition is dried.

For the use throughout this document a cermet precursor composition is a composition from which by firing a cermet can be obtained. For the use throughout this document a ceramic green sheet is a ceramic precursor sheet, wherein by firing the ceramic precursor sheet a ceramic sheet can be prepared.

In an embodiment, the process includes as further process steps
a) providing a further ceramic green sheet, comprising a further hole and a further ceramic green sheet surface,
wherein the further hole has a further hole volume;
b) providing a further plurality of portions of a further cermet precursor composition,
wherein the further plurality of portions of the further cermet precursor composition has a total further cermet precursor composition volume,
wherein the total further cermet precursor composition volume is higher than the further hole volume;
c) filling the further plurality of portions of the further cermet precursor composition into the further hole in subsequent fill-in steps portion by portion,
wherein after each fill-in step a filled in portion of the further cermet precursor composition is dried;
d) contacting the first ceramic green sheet surface with the further ceramic green sheet surface, wherein the first hole and the further hole are contacted;
e) firing the first ceramic green sheet and the further ceramic green sheet.

In an embodiment, the first cermet precursor composition, or the further cermet precursor composition, or both includes
a) Pt in the range from 60 wt.-% to the remainder completing the sum of all components to 100 wt.-%, in one embodiment in the range from 65 wt.-% to the remainder completing the sum of all components to 100 wt.-%, in one embodiment in the range from 70 wt.-% to the remainder completing the sum of all components to 100 wt.-%, in one embodiment in the range from 80 wt.-% to the remainder completing the sum of all components to 100 wt.-%,
b) $Al_2O_3$ in the range from 0.5 to 25 wt.-%, in one embodiment in the range from 0.5 to 20 wt.-%, in one embodiment in the range from 1 to 15 wt.-%, in one embodiment in the range from 1.1 to 8 wt.-%, in one embodiment in the range from 1.7 to 4.5 wt.-%,
c) a vehicle in the range from 8 to 30 wt.-%, in one embodiment in the range from 9 to 28 wt.-%, in one embodiment in the range from 9 to 22 wt.-%, in one embodiment in the range from 9 to 12 wt.-%
each based on the total weight of the first cermet precursor composition or the further cermet precursor composition.

In an embodiment, the contacting of the first ceramic green sheet surface with the further ceramic green sheet surface is a laminating.

In an embodiment, a filling is one selected from the group consisting of a printing, an injecting, and a depositing, or a combination of at least two thereof.

In one embodiment, a printing is a screen printing or a stencil printing or both. In one embodiment depositing is a physical depositing or a chemical depositing or both. In one embodiment physical depositing is a physical vapour depositing. In one embodiment chemical depositing is a chemical vapour depositing.

In an embodiment, during at least one of the fillings into the first hole a vacuum is present in the first hole. Therein, a vacuum includes a pressure which is at least 10%, in one embodiment at least 15%, in one embodiment at least 20%, in one embodiment at least 30%, in one embodiment at least 40%, in one embodiment at least 50%, in one embodiment at least 60%, lower than the pressure of the ambient air outside of the first hole, based on the ambient air pressure outside of the first hole.

In an embodiment, during at least one of the fillings into the further hole a vacuum is present in the further hole. Therein, a vacuum includes a pressure which is at least 10%, in one embodiment at least 15%, in one embodiment at least 20%, in one embodiment at least 30%, in one embodiment at least 40%, in one embodiment at least 50%, in one embodiment at least 60%, lower than the pressure of the ambient air outside of the further hole, based on the ambient air pressure outside of the further hole.

In an embodiment, the contacting of the first ceramic green sheet surface with the further ceramic green sheet surface is a pressing the first ceramic green sheet surface and the further ceramic green sheet surface onto each other by applying a pressure in the range from 100 to 500 bar, in one embodiment in the range from 150 to 450 bar, in one embodiment in the range from 200 to 400 bar, in one embodiment in the range from 300 to 400 bar.

A contribution to the solution of at least one of the above is made by a composite obtainable by the process according to one embodiment.

A contribution to the solution of at least one of the above is made by a device; comprising a hollow body, an inner volume, an outer volume, and the composite according to one embodiment;
  wherein the hollow body
  a) encloses the inner volume,
  b) separates the inner volume from the outer volume,
  c) includes an aperture;
  wherein the aperture includes the composite;
  wherein the composite electrically connects the inner volume to the outer volume.

In one embodiment, a device is an electrical device. In one embodiment, an electrical device is an implantable electrical device. In one embodiment, an implantable electrical device is a medical implantable electrical device. In one embodiment the cermet element or at least one further cermet element or both electrically connects the inner volume to the outer volume. In one embodiment, the cermet element and each further cermet element electrically connect the inner volume to the outer volume.

A contribution to the solution of at least one of the above is made by a device; comprising a hollow body, an inner volume, an outer volume, and the composite according to one embodiment;
  wherein the hollow body
  a) encloses the inner volume,
  b) separates the inner volume from the outer volume,
  c) includes an aperture;
  wherein the aperture frames the composite;
  wherein the blind hole end face is included by the inner volume. In one embodiment, the blind hole front face is included by the outer volume. In one embodiment, a device is an electrical device. In one embodiment, an electrical device is an implantable electrical device. In one embodiment, an implantable electrical device is a medical implantable electrical device.

In one embodiment, a device is one selected from the group consisting of a pacemaker, a neuro-stimulator, a measuring device and a defibrillator or a combination of at least two thereof. In an embodiment, a pacemaker is one selected from the group consisting of a bladder pacemaker, a breath pacemaker, an intestinal pacemaker, a diaphragm pacemaker, a cerebral pacemaker and a cardiac pacemaker or a combination of at least two thereof. In an embodiment, a pacemaker is a cardiac pacemaker. In an embodiment, a measuring device is a biomonitor. In an embodiment, a device is a biomonitor.

A contribution to the solution of at least one of the above is made by a use of a plurality of ceramic green sheets and a composition to produce a composite according one embodiment;
  wherein the composition includes
  a) Pt in the range from 60 wt.-% to the remainder completing the sum of all components to 100 wt.-%, in one embodiment in the range from 65 wt.-% to the remainder completing the sum of all components to 100 wt.-%, in one embodiment in the range from 70 wt.-% to the remainder completing the sum of all components to 100 wt.-%, in one embodiment in the range from 80 wt.-% to the remainder completing the sum of all components to 100 wt.-%,
  b) $Al_2O_3$ in the range from 0.5 to 25 wt.-%, in one embodiment in the range from 0.5 to 20 wt.-%, in one embodiment in the range from 1 to 15 wt.-%, in one embodiment in the range from 1.1 to 8 wt.-%, in one embodiment in the range from 1.7 to 4.5 wt.-%,
  c) a vehicle in the range from 8 to 30 wt.-%, in one embodiment in the range from 9 to 28 wt.-%, in one embodiment in the range from 9 to 22 wt.-%, in one embodiment in the range from 9 to 12 wt.-%, each based on the total weight of the composition.

Hole

The term "hole" used in this paragraph refers to the hole, the further holes as well as the first hole, each according to one embodiment. In one embodiment, a hole includes a front face in a first surface of the layer sequence, wherein the first surface faces away from the layer sequence; an end face; and a lateral surface connecting the front face to the end face. Therein, a preferred end face is located in a further surface of the layer sequence, wherein the further surface faces away from the layer sequence and is positioned opposite to the first surface of the layer sequence. In one embodiment, end face is located in one selected from the group consisting of a surface of the ceramic body layer, a surface of one of the further ceramic body layers, the lateral surface of the blind hole according to one embodiment or a combination of at least two thereof. Therein, each of the front face and the end face and a transversal cross section of the lateral surface of the hole can have any shape of a geometrical surface that seems applicable according to one embodiment to the skilled person. In one embodiment, front face is about cyclic. In one embodiment, end face is about cyclic. In one embodiment, lateral surface of the hole is at least partly about cylindrical. In one embodiment, lateral surface of the hole is about prism shaped.

Blind Hole

In one embodiment, blind hole includes a blind hole front face; an end face; and a lateral surface connecting the blind hole front face to the blind hole end face. Therein, the blind hole front face is an opening in the body surface of the ceramic body. The blind hole end face is included by the ceramic body. This means the blind hole end face is not an opening in a surface of the ceramic body, but the blind hole end face is at least a part of a surface of the ceramic body. Therein, the blind hole front face and the blind hole end face and a transversal cross section of the lateral surface can have any shape of a geometrical surface that seems applicable according to one embodiment to the skilled person. In one embodiment, a blind hole front face is about cyclic. In one embodiment, blind hole end face is about cyclic. In one embodiment, lateral surface is at least partly about a lateral surface of a cylinder. In one embodiment, lateral surface is at least partly about a lateral surface of a prism. In one embodiment, a blind hole is designed to accommodate a lead. Therein, a lead being plugged through the blind hole front face into the blind hole is preferably electrically connected to the cermet element, or at least one further cermet element, preferably each further cermet element, or both.

Layer

The term "layer" used in this paragraph includes any layer according to one embodiment. For the use throughout this document a layer superimposes a layer surface of another layer if the layer follows the other layer in the direction which the layer surface faces. A layer which superimposes a layer surface may be bonded to the layer surface. In one embodiment, a bond is a physical bond or a chemical bond or both. A layer which superimposes a layer surface may follow the layer surfaces directly or there may be additional layers, substances or objects between the layer and the layer surface which is superimposed by the layer. Any layer may include sublayers.

Cermet

According to one embodiment a cermet is a composite material, comprising at least one ceramic component in at least one metallic matrix; or a composite material, comprising at least one metallic component in a least one ceramic matrix; or both. At least one ceramic powder and at least one metallic powder can for example be applied for preparing a cermet, wherein to at least one of the powders for example a binder can be added and optionally at least one surfactant. The ceramic powder/the ceramic powders of the cermet in one embodiment have an average grain size of less than 10 μm, in one embodiment less than 5 μm, in one embodiment less than 3 μm. In some cases the ceramic powder of the cermet has an average particle size of at least 15 μm. The metallic powder/the metallic powders of the cermet in one embodiment have an average grain size of less than 15 μm, in one embodiment less than 10 μm, in one embodiment less than 5 μm. Therein, the average grain size is particularly the median value or the $D_{50}$. The $D_{50}$ gives the value, at which 50% of the grains of the ceramic powder and/or the metallic powder are smaller than the $D_{50}$. In one embodiment, cermet is characterised by a high specific conductivity, which is in one embodiment at least 1 S/m, in one embodiment at least $10^3$ S/m, in one embodiment at least $10^4$ S/m, in one embodiment at least $10^5$ S/m, in one embodiment at least $10^6$ S/m. The at least one ceramic component of the cermet according to one embodiment includes a ceramic. The at least one metallic component of the cermet according to one embodiment includes one selected from the group consisting of platinum, iridium, niobium, palladium, iron, stainless steel, a cobalt-chromium-alloy, molybdenum, tantalum, tungsten, titanium, cobalt and zirconium or a combination of at least two thereof. Therein a preferred combination is an alloy. In one embodiment, a stainless steel is stainless steel 316L. Generally, the cermet becomes electrically conductive if the metal content of the cermet is above the so called percolation threshold, at which metal particles in the sintered cermet are at least partly connected to each other in such a way that electrical charges can be transported via conduction. Therefore, the metal content of the cermet should according to experience depending on the choice of materials be at least 25 vol.-%, in one embodiment at least 32 vol.-%, in one embodiment at least 38 vol.-%, each based on the total volume of the cermet.

Ceramic

A ceramic according to one embodiment can be any ceramic the skilled person deems applicable to the embodiment. The ceramic is in one embodiment selected from the group consisting of an oxide ceramic, a silicate ceramic and a non-oxide ceramic or a combination of at least two thereof.

The oxide ceramic includes in one embodiment a metal oxide or a metalloid oxide or both. A metal of the metal oxide is in one embodiment selected from the group consisting of aluminum, beryllium, barium, calcium, magnesium, sodium, potassium, iron, zirconium, titanium, or a combination of at least two thereof. In one embodiment, a metal oxide is selected from the group consisting of aluminum oxide ($Al_2O_3$); magnesium oxide (MgO); zirconium oxide ($ZrO_2$); yttrium oxide ($Y_2O_3$); aluminum titanate ($Al_2TiO_5$); a piezoceramic as for example lead-zirconate ($PbZrO_3$), lead-titanate ($PbTiO_3$) and lead-zirconate-titanate (PZT); or a combination of at least two thereof. In one embodiment, a metalloid of the metalloid oxide is selected from the group consisting of boron, silicon, arsenic, tellurium, or a combination of at least two thereof. In one embodiment, an oxide ceramic includes one selected from the group consisting of aluminum oxide toughened with zirconium oxide enhanced (ZTA—Zirconia Toughened Aluminum—$Al_2O_3/ZrO_2$), zirconium oxide toughened with yttrium (Y-TZP), barium(Zr, Ti)oxide, barium(Ce, Ti)oxide or a combination of at least two thereof.

The silicate ceramic is in one embodiment selected from the group consisting of a steatite ($Mg_3[Si_4O_{10}(OH)_2]$), a cordierite ($(Mg, Fe^{2+})_2(Al_2Si)[Al_2Si_4O_{18}]$), a mullite ($Al_2Al_{2+2x}Si_{2-2x}O_{10-x}$ with x=oxide defects per unit cell), a feldspar ($(Ba,Ca,Na,K,NH_4)(Al,B,Si)_4O_8$) or a combination of at least two thereof.

The non-oxide ceramic in one embodiment includes a carbide or a nitride or both. In one embodiment, a carbide is one selected from the group consisting of silicon carbide (SiC), boron carbide ($B_4C$), titanium carbide (TiC), tungsten carbide, cementite ($Fe_3C$) or a combination of at least two thereof. In one embodiment, a nitride is one selected from the group consisting of silicon nitride ($Si_3N_4$), aluminum nitride (AlN), titanium nitride (TiN), silicon aluminum oxinitride (SIALON) or a combination of at least two thereof. In one embodiment a non-oxide ceramic is sodium-potassium-niobate.

Thickness

For the use throughout this document a thickness of a $m^{th}$ part of a cermet element, wherein m is an integer of at least 2, is a maximum length over which the part extends in a direction perpendicular to a surface of a layer of the layer sequence, wherein the part is adjacent to said layer.

Length

The term "cermet element" used in this paragraph includes the cermet element as well as the further cermet elements according to one embodiment. The term "hole" used in this paragraph includes the holes as well as the further holes and the first hole, each according to one embodiment. For the use throughout this document a length of a $k^{th}$ part of a cermet element, wherein k is an integer of at least 2, is defined in a cross sectional plane between two layer surfaces of the layer sequence adjacent to the part. Therein, the $k^{th}$ part and a first part are included by the cermet element. Therein, the first part is included by a hole. In said plane said length of the $k^{th}$ part is a length of a longest straight line along a radius of the hole, connecting a geometric centre of the hole to a point of the $k^{th}$ part, minus the length of the radius of the hole.

Radius

The term "hole" used in this paragraph includes the holes as well as the further holes and the first hole, each according to one embodiment. For the use throughout this document a radius of a hole is a shortest straight line in a transversal cross sectional plane of the hole connecting a geometric centre of the hole to a lateral surface of the hole.

Diameter

The term "hole" used in this paragraph includes the holes as well as the further holes and the first hole, each according to one embodiment. For the use throughout this document a diameter of a hole is a shortest straight line in a transversal cross sectional plane of the hole, connecting two positions on a lateral surface of the hole, wherein the straight line includes a geometric centre of the hole.

Drying

In one embodiment, a drying includes a peak temperature in the range from 50 to 500° C., in one embodiment in the range from 70 to 400° C., in one embodiment in the range from 100 to 300° C., in one embodiment in the range from 100 to 200° C. In one embodiment, drying is performed for at least 3 minutes, in one embodiment for at least 4 minutes, in one embodiment for at least 5 minutes, in one embodiment for at least 7 minutes, in one embodiment for at least 10 minutes.

Firing

Firing can be performed in any oven the skilled person deems appropriate for firing the respective green sheet. In one embodiment, firing is performed in a box oven. In one embodiment, firing includes a peak temperature in the range from 1000 to 2000° C., in one embodiment in the range from 1250 to 1900° C., in one embodiment in the range from 1510 to 1650° C. In one embodiment, firing includes keeping a peak temperature constant for a duration in the range from 0.3 to 10 hours, in one embodiment in the range from 0.5 to 7 hours, in one embodiment in the range from 1 to 5 hours.

Test Methods

The following test methods are used in one embodiment. In absence of a test method, the ISO test method for the feature to be measured being closest to the earliest filing date of the present application applies. In absence of distinct measuring conditions, standard ambient temperature and pressure (SATP) as a temperature of 298.15 K (25° C., 77° F.) and an absolute pressure of 100 kPa (14.504 psi, 0.986 atm) apply.

Layer Thickness

The layer thickness is measured using a micrometre screw gauge. Therein, the measuring spindle of the micrometre is screwed slowly towards the probe applying the ratchet. The ratchet limits the force applied by the measuring spindle to the probe to 5 to 10 N. For the measurement the micrometre is fixed to a tripod in order to prevent distortions due to warmth from a hand.

Volume of Holes

The volume of the hole is determined geometrically as the product of the layer thickness and the area of the hole opening. Therein, the area is determined as $\pi \cdot d^2/4$ for a circular hole opening, wherein d is the diameter of the hole opening. d can be measured using an optical microscope.

Volume of Cermet Precursor Composition

The volume of the wet cermet precursor composition applied to a hole is determined as the sum of the volume of the screen aperture or stencil aperture used to apply the composition by screen or stencil printing and the volume of the hole. Therein, the volume of the aperture of the screen or stencil is determined geometrically. The volume of the screen or stencil aperture is the product of the thickness of the screen or stencil and the area of the aperture. Therein, the area is determined as $\pi \cdot d^2/4$ for a circular aperture, wherein d is the diameter of the aperture. d can be measured using an optical microscope.

Leak Testing

A quantity which may describe for example a permeation of gases or moisture or both is the so called leak rate. The leak rate may be measured in a leak test. A leak test may be performed using a helium leak tester and/or a mass spectrometer. Such a leak test is standardised in Mil-STD-883G method 1014. Therein, a maximum tolerable helium leak rate is determined depending on an internal volume of the device to be tested. According to the methods specified in paragraph 3.1 of MIL-STD-883G, method 1014, and considering the relevant volumina and cavities of the devices to be tested in the context of one embodiment the maximum tolerable helium leak rates could for example be in the range from $1 \times 10^{-8}$ atm×cm³/s to $1 \times 10^{-7}$ atm×cm³/s. In terms of standardising, the helium leak rates may be converted into the equivalent standard air leak rates. The definition of the equivalent standard air leak rate and the method of conversion are given in the standard ISO 3530. An implantable medical device is usually used within a human or animal body. Therefore, leak tightness and biocompatibility are commonly the main requirements that the device has to match. Implanted in a human or animal body the device usually is exposed to a fluid of a tissue of the body. Therefore, it is usually important that neither a body fluid penetrates into the housing of the device nor a fluid penetrates out of the housing. In order to ensure this, the housing should be as impenetrable as possible, for example, with regard to body fluids.

Viscosity

Viscosity measurements were performed using the Thermo Fischer Scientific Corp. "Haake Rheostress 6000" equipped with a ground plate MPC60 Ti and a cone plate C 20/0,5° Ti and software "Haake RheoWin Job Manager 4.00.0007". After setting the distance zero point, a paste sample sufficient for the measurement was placed on the ground plate. The cone was moved into the measurement positions with a gap distance of 0.049 mm and excess material was removed using a spatula. The sample was equilibrated to 25° C. for three minutes and the rotational measurement started. The shear rate was increased from 0 to 15 s-1 within 60 s and 30 equidistant measuring points. After a waiting time of 60 s at a shear rate of 15 s-1, the shear rate was reduced from 15 to 0 s-1 within 60 s and 30 equidistant measuring points. The micro torque correction, micro stress control and mass inertia correction were activated. The viscosity is given as the measured value at a shear rate of 5 s-1 of the downward shear ramp.

Scanning Electron Microscopy (SEM)

The sample is cut in a way that the area of interest is laid open. In this case perpendicular to the surface of the substrate so that a cross section of the different layers was obtained. The cut sample is placed in a container filled with embedding material and oriented such that the area of interest is on top. As embedding material, EpoFix (Struers GmbH) is used, mixed according to the instructions. After 8 hours curing at room temperature the sample can be processed further. In a first step the sample is ground with a Labopol-25 (Struers GmbH) using silicon carbide paper 180-800 (Struers GmbH) at 250 rpm. In further steps the sample is polished using a Rotopol-2 equipped with a Retroforce-4, MD Piano 220 and MD allegro. The SEM analysis is performed with a Zeiss Ultra 55 (Carl Zeiss AG), equipped with a field emission electrode, an accelerating voltage of 20 kV and at a pressure of about 3×10-6 mbar. In some cases the cross sections were used to determine the elemental composition along a line across the different layers and perpendicular to the substrate surface. So called line scan was performed using an EDX measurement (energy dispersive X-ray spectroscopy). An IncaPentaFETx3 attached to the Zeiss Ultra 55 and the software "The Microanalysis Suite Issue 18d+ SP3" (both from Oxford Instruments) with an aperture of 30 μm were used.

EXAMPLES

The present embodiments are now explained in more detail by examples and drawings given by way of example, wherein the examples and drawings do not limit the embodiments.

Paste Recipe 60 g of Pt powder were mixed with 24 g of aluminum oxide powder and a cellulose solvent based organic vehicle and homogenised with a three roll mill. The pastes exhibited a rheology that was suitable for stencil printing.

Ceramic Green Sheet Preparation

A ceramic green tape was used as the ceramic green sheet. The ceramic tape used was a 99.7% high purity alumina tape. The green tape thickness was 400 μm. Green tape samples were cut to 90 mm×90 mm squares. About circular holes of 400 m in diameter were punched into the green tape using a 400 μm diameter mechanical punch in an automatic puncher machine.

Filling

The filling of the holes was performed using a stencil with a specific pattern on an EKRA Microtronic II printer (type M2H). The stencil thickness was 100 μm. The stencil openings had the same dimensions and location as the holes punched through the ceramic green tape. The squeegee cycle was set so that cermet material would be deposited in both the forward and backward squeegee movements. Thereby, a filling of approximately 200 μm thickness after printing (wet), approximately 150 μm thickness after drying was achieved. The filling step was repeated a minimum of 3 times until a satisfactory amount of material was deposited in all holes.

Drying 10 minutes after printing the samples were placed in a drying apparatus and dried at 150° C. for 10 minutes.

Laminating 3 to 7 layers of green tape with the holes filled according to the above process were stacked using a metal aligning tool and isostatically pressed under 350 bar of pressure in an oil bath at elevated temperature in order to achieve the desired component thickness.

Drilling

The drilling was optimum, at green state, with a feed rate of 100 mm/min. Return stroke was used. Thereby, a hole contacting the cermet channel through the laminated green sheets as indicated in FIG. 17a was obtained. Said drilled hole was closed by a plug in order to withstand the following processing steps. Therein, the material and dimensions of the plug were chosen to minimise stresses due to the following firing steps and to allow for easy removal after firing.

Firing

The resulting laminate of green tapes was fired in a high temperature box oven capable of providing a peak temperature of 1750° C. with a firing chamber of size 200 mm×250 mm×200 mm. The firing took place under normal atmosphere conditions. The temperature was increased to 450° C. in order to burn away organic components remaining in the green laminate. Subsequently, the temperature was increased to a peak temperature in the range from 1510 to 1650° C. and then kept at that temperature for a period of time in the range from 1 to 5 hours. Subsequently, the temperature was decreased to room temperature.

Post-firing Processing

After the end of the firing process the plug was removed and the samples were ground and cut to the desired dimensions by laser cutting.

FIG. 1a illustrates a schematic cross sectional side view of a composite 100 according to one embodiment. The composite 100 includes a layer sequence 101. The layer sequence 101 includes a first layer 102, comprising a first ceramic and a first layer surface 103, and a second layer 104, comprising a second ceramic. Therein, the second layer 104 superimposes the first layer surface 103. The first ceramic is Al2O3. The second ceramic is Al2O3. The layer sequence 101 further includes a hole 105, wherein the hole 105 connects through the first layer 102 and the second layer 104. The hole 105 is about cylindrically shaped. The layer sequence 101 further includes a cermet element 106, which consists of a first part 107 and a second part 108. Therein, the first part 107 is included by the hole 105. Hence, the first part 107 is about cylindrical. The second part 108 is included between the first layer 102 and the second layer 104. The second part 108 is adjacent to the first layer surface 103. Moreover, the second part 108 is adjacent to the first part 107. The first part 107 and the second part 108 form the cermet element 106 which is in one piece. The cermet element 106 has a shape similar to a backbone or a bamboo or both. The cermet element 106 includes a cermet, wherein the cermet includes 97 wt.-% Pt and 3 wt.-% Al2O3, each based on the total weight of the cermet element 106.

Figure 1B:
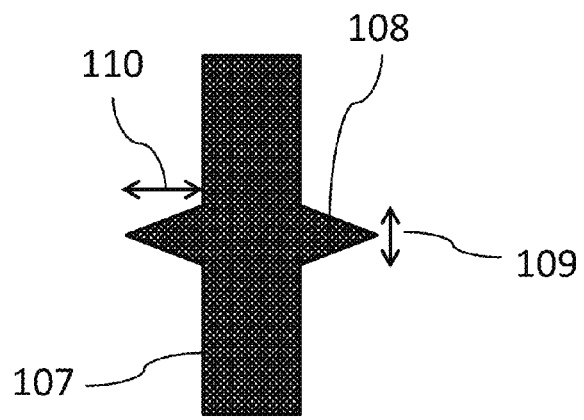

FIG. 1b illustrates a detailed scheme of the cermet element 106 of FIG. 1a. Therein, the second part 108 has a thickness at its widest portion 109 of 5 μm. Moreover, the second part 108 has a length 110 of 50 μm.

Figure 2:
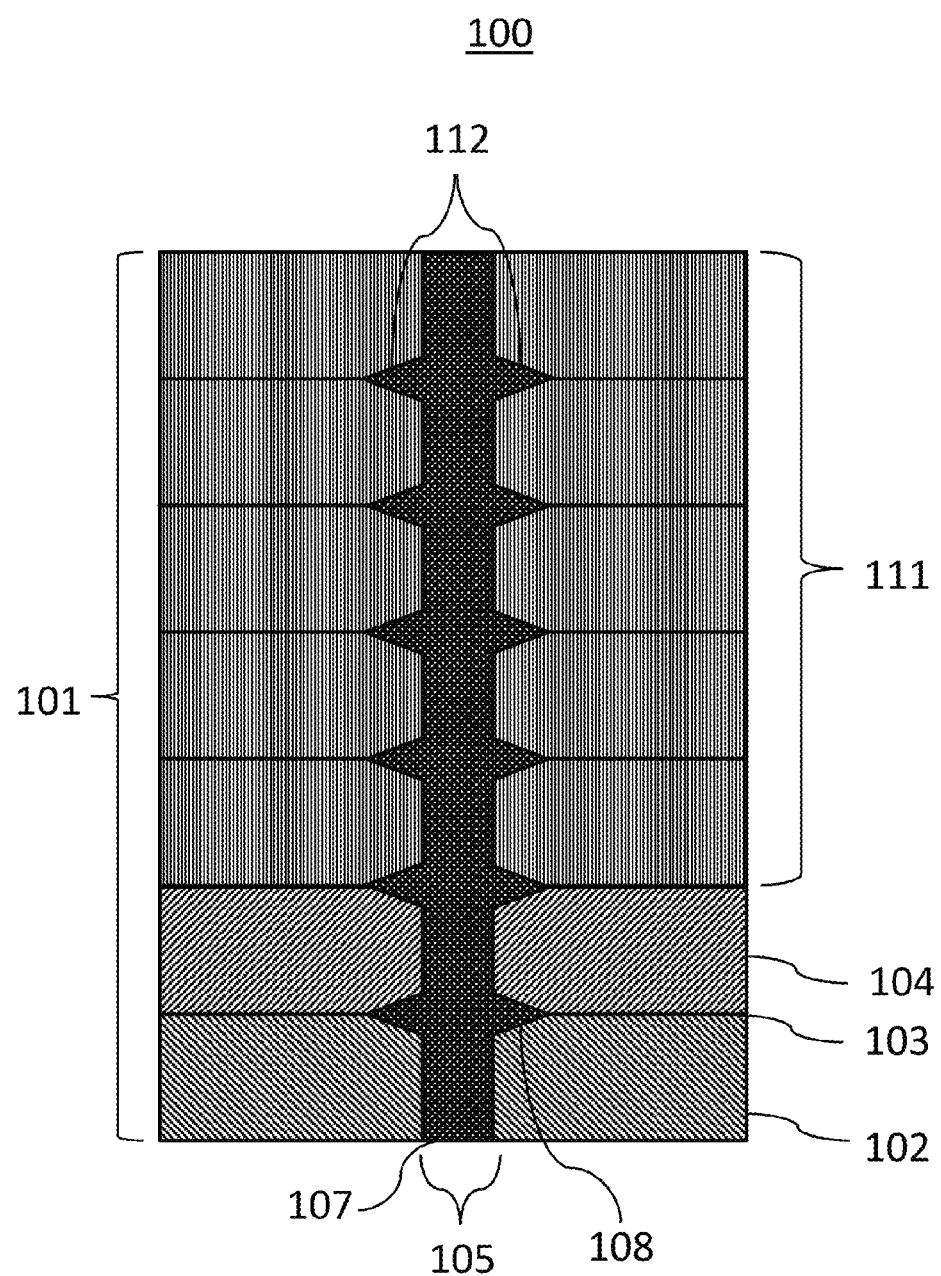
FIG. 2 is a schematic cross sectional side view of another composite according to one embodiment.

FIG. 2 illustrates a schematic cross sectional side view of another composite 100 according to one embodiment. The composite 100 includes a layer sequence 101. The layer sequence 101 includes a first layer 102, comprising a first ceramic and a first layer surface 103, and a second layer 104, comprising a second ceramic. Therein, the second layer 104 superimposes the first layer surface 103. The first ceramic is $Al_2O_3$. The second ceramic is $Al_2O_3$. The layer sequence 101 further includes n layers 111. Each $i^{th}$ layer of the layer sequence 101 includes an $i^{th}$ ceramic. Each $i^{th}$ ceramic is Al$_2$O$_3$. Each i$^{th}$ layer of the layer sequence 101 further includes an i$^{th}$ layer surface. Therein, each i$^{th}$ layer superimposes the (i−1)$^{th}$ layer surface. The layer sequence 101 further includes a hole 105, wherein the hole 105 connects through each layer 102, 104, 111 of the layer sequence 101. The hole 105 is about cylindrically shaped. The layer sequence 101 further includes a cermet element 106, which consists of a first part 107 and a second part 108 and further n parts 112. Therein, the first part 107 is included by the hole 105. Hence, the first part 107 is about cylindrical. Each i$^{th}$ part 108, 112 of the cermet element 106 is included between the i$^{th}$ layer and the (i−1)$^{th}$ layer of the layer sequence 101. Each i$^{th}$ part 108, 112 is adjacent to the first part 107. Here n equals 5 and i can be any integer in the range from 2 to 7. The cermet element 106 is in one piece. The cermet element 106 has a shape similar to a backbone or a bamboo or both. The cermet element 106 includes a cermet, wherein the cermet includes 97 wt.-% Pt and 3 wt.-% Al$_2$O$_3$, each based on the total weight of the cermet element 106.

Figure 3A:
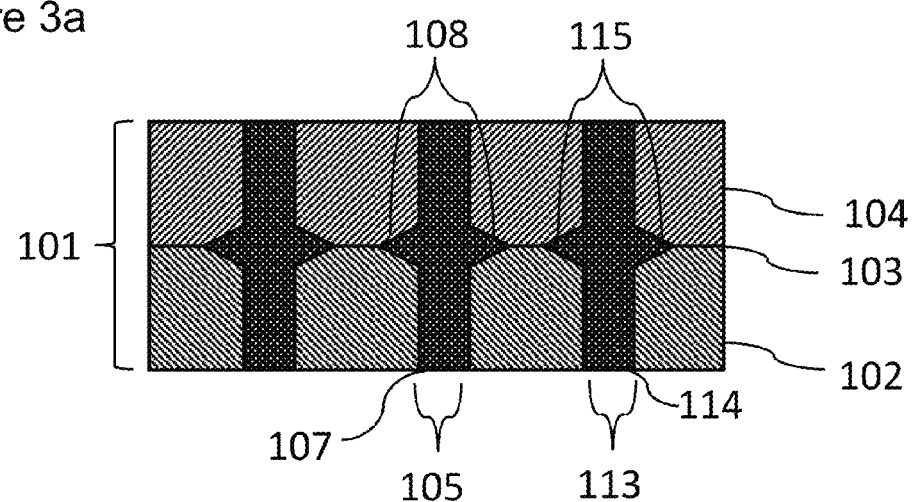
FIG. 3a is a schematic cross sectional side view of another composite according to one embodiment.

FIG. 3a illustrates a schematic cross sectional side view of another composite 100 according to one embodiment. The composite 100 includes a layer sequence 101. The layer sequence 101 includes a first layer 102, comprising a first ceramic and a first layer surface 103, and a second layer 104, comprising a second ceramic. Therein, the second layer 104 superimposes the first layer surface 103. The first ceramic is Al$_2$O$_3$. The second ceramic is Al$_2$O$_3$. The layer sequence 101 further includes a hole 105, wherein the hole 105 connects through the first layer 102 and the second layer 104. The hole 105 is about cylindrically shaped. The layer sequence 101 further includes a cermet element 106, which consists of a first part 107 and a second part 108. Therein, the first part 107 is included by the hole 105. Hence, the first part 107 is about cylindrical. The second part 108 is included between the first layer 102 and the second layer 104. The second part 108 is adjacent to the first layer surface 103. Moreover, the second part 108 is adjacent to the first part 107. The first part 107 and the second part 108 form the cermet element 106 which is in one piece. The cermet element 106 has a shape similar to a backbone or a bamboo or both. The cermet element 106 includes a cermet, wherein the cermet includes 97 wt.-% Pt and 3 wt.-% Al$_2$O$_3$, each based on the total weight of the cermet element 106. The layer sequence 101 further includes two further holes 113. Each further hole 113 connects through the first layer 102 and the second layer 104. Each further hole 113 is about cylindrically shaped. Moreover, the layer sequence 101 further includes two further cermet elements 117. Each further cermet element 117 consists of a further first part 114 and a further second part 115. Each further first part 114 is included by one of the further holes 113. Hence, each further first part 114 is about cylindrical. Each further second part 115 is included between the first layer 102 and the second layer 104. Each further second part 115 is adjacent to a further first part 114 and the first layer surface 103. Each further cermet element 117 is in one piece. Each further cermet element 117 includes a cermet, wherein the cermet includes 97 wt.-% Pt and 3 wt.-% Al$_2$O$_3$, each based on the total weight of the further cermet element 117. Each further cermet element 117 has a shape similar to a backbone or a bamboo or both.

Figure 3B:
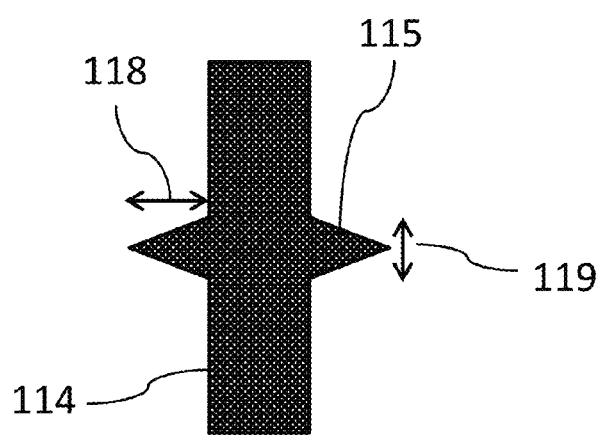

FIG. 3b illustrates a detailed scheme of one of the further cermet elements 117 of FIG. 3a. Therein, the further second part 115 has a thickness at its widest portion 119 of 5 μm. Moreover, the further second part 115 has a length 118 of 50 μm.

Figure 4:
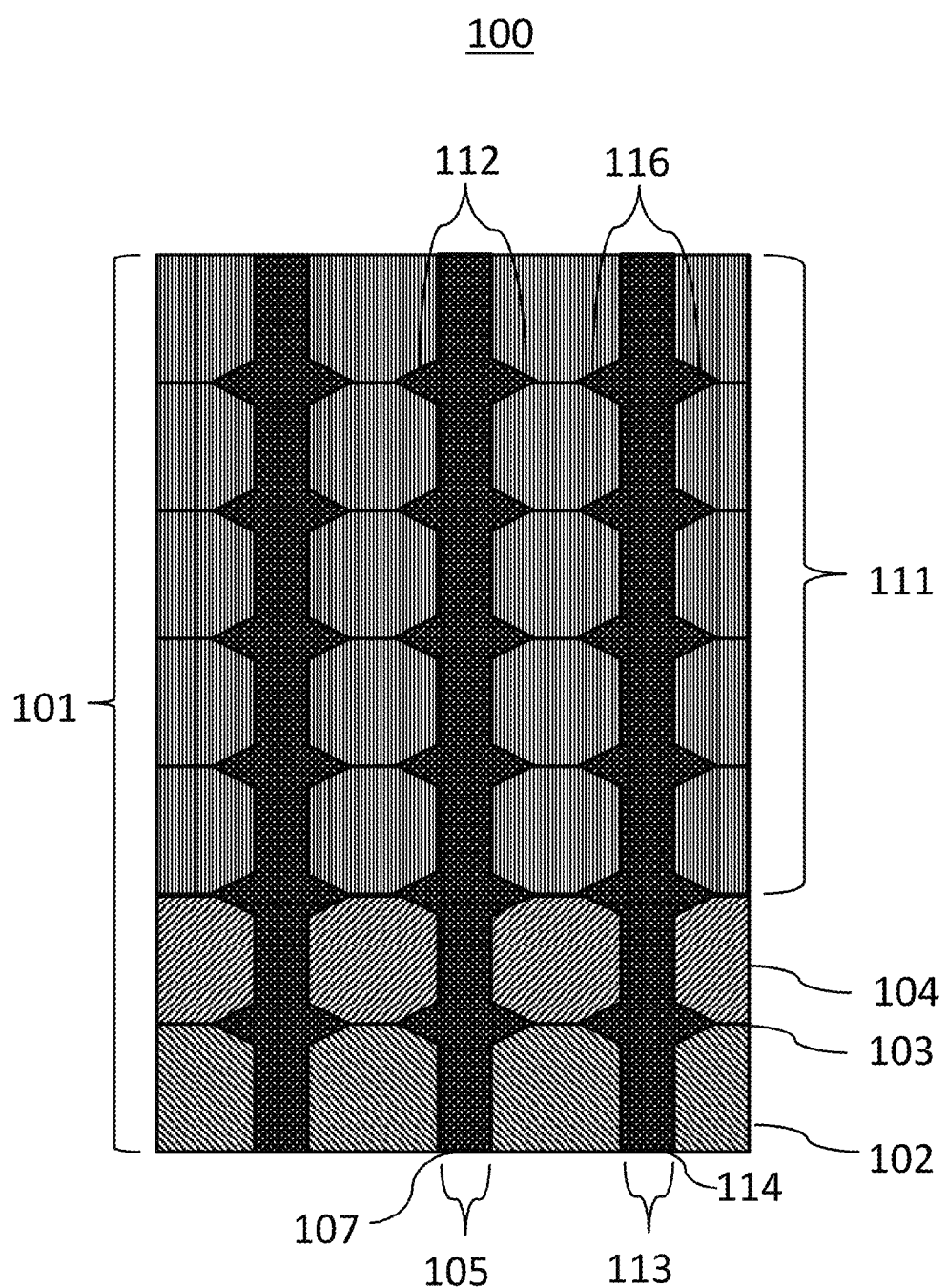
FIG. 4 is a schematic cross sectional side view of another composite according to one embodiment.

FIG. 4 illustrates a schematic cross sectional side view of another composite 100 according to one embodiment. The composite 100 is identical to the composite 100 of FIG. 2 with the exception of the layer sequence 101 of the composite 100 of FIG. 4 additionally comprising two further holes 113. Each further hole 113 connects through each layer 102, 104, 111 of the layer sequence 101. Each further hole 113 is about cylindrically shaped. Moreover, the layer sequence 101 further includes two further cermet elements 117. Each further cermet element 117 includes a further first part 114 and a further second part 115. Each further first part 114 is included by one of the further holes 113. Hence, each further first part 114 is about cylindrical. Each further cermet element 117 consists in total of (n+2)=7 further parts 114, 115, 116. Each further i$^{th}$ part 115, 116 is included between the i$^{th}$ layer and the (i−1)$^{th}$ layer. Each further i$^{th}$ part 115, 116 is adjacent to a further first part 114 and the first layer surface 103. Each further cermet element 117 is in one piece. Each further cermet element 117 includes a cermet, wherein the cermet includes 97 wt.-% Pt and 3 wt.-% Al$_2$O$_3$, each based on the total weight of the further cermet element 117. Each further cermet element 117 has a shape similar to a backbone or a bamboo or both.

Figure 5:
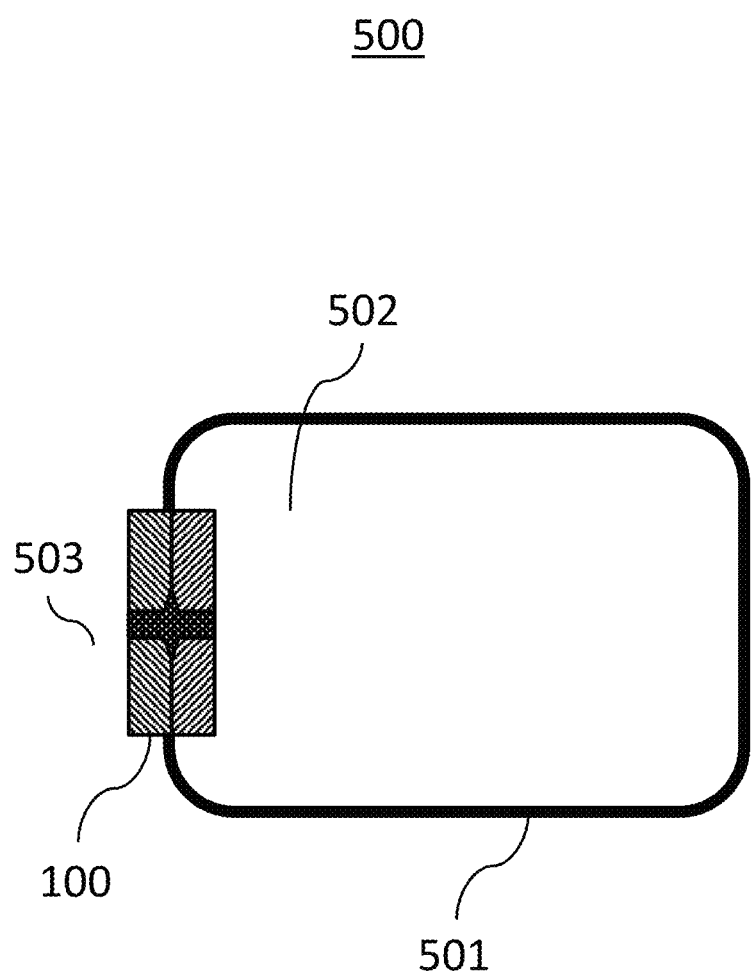
FIG. 5 is a schematic cross sectional side view of a device according to one embodiment.

FIG. 5 illustrates a schematic cross sectional side view of a device 500 according to one embodiment. The device 500 includes a hollow body 501, here a metal housing 501; an inner volume 502; and an outer volume 503; and the composite 100 of FIG. 1a. Therein, the metal housing 501 is made of a titanium alloy which is biocompatible and suitable for medical applications. Furthermore, the metal housing 501 encloses the inner volume 502, separates the inner volume 502 from the outer volume 503, and includes an aperture. The aperture includes the composite 100. The connection between the aperture and the composite 100 is sealed by soldering. The device 500 is a biomonitor.

Figure 6:
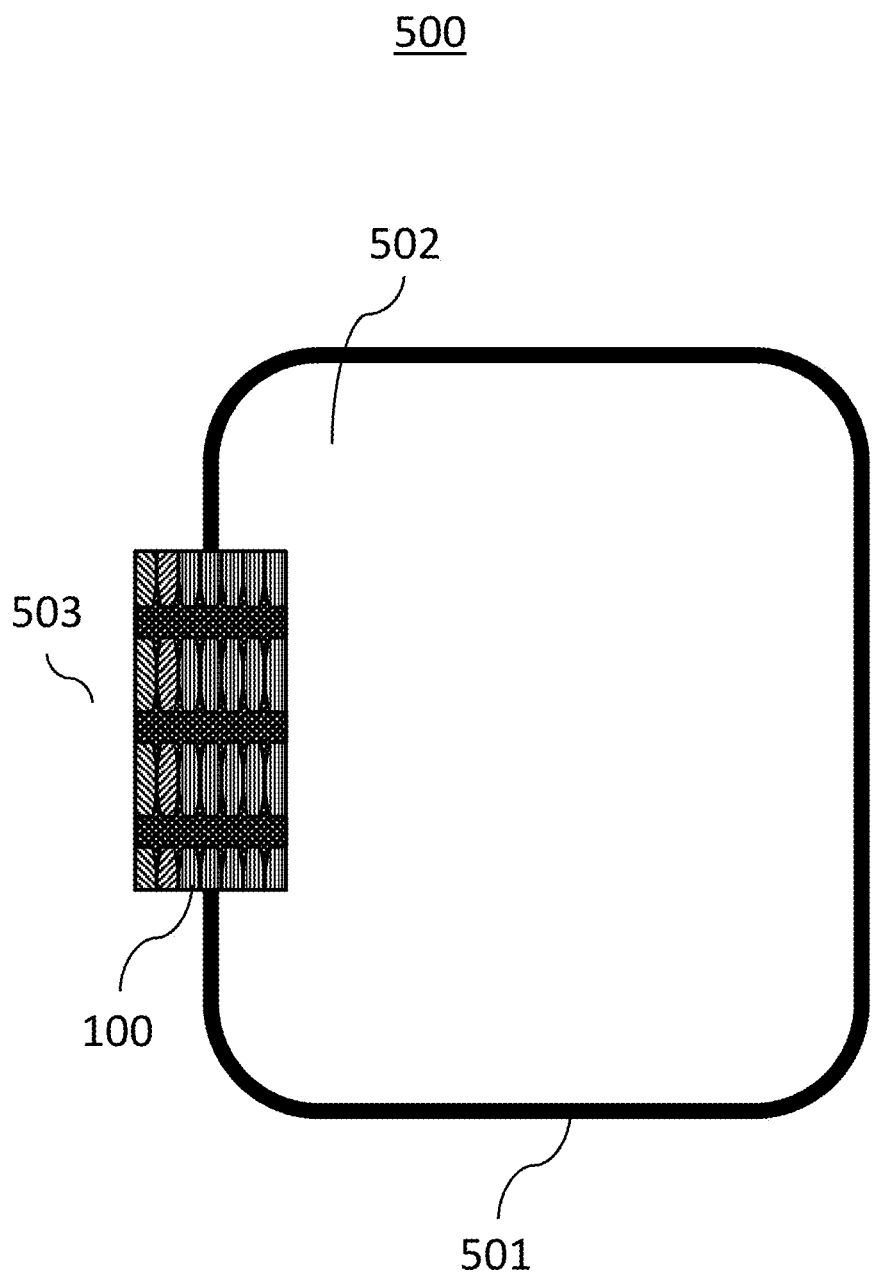
FIG. 6 is a schematic cross sectional side view of another device according to one embodiment.

FIG. 6 illustrates a schematic cross sectional side view of another device 500 according to one embodiment. The device 500 includes a hollow body 501, here a metal housing 501; an inner volume 502; and an outer volume 503; and the composite 100 of FIG. 4. Therein, the metal housing 501 is made of a titanium alloy which is biocompatible and suitable for medical applications. Furthermore, the metal housing 501 encloses the inner volume 502, separates the inner volume 502 from the outer volume 503, and includes an aperture. The aperture includes the composite 100. The connection between the aperture and the composite 100 is sealed by soldering. The device 500 is a cardiac pacemaker.

Figure 7:
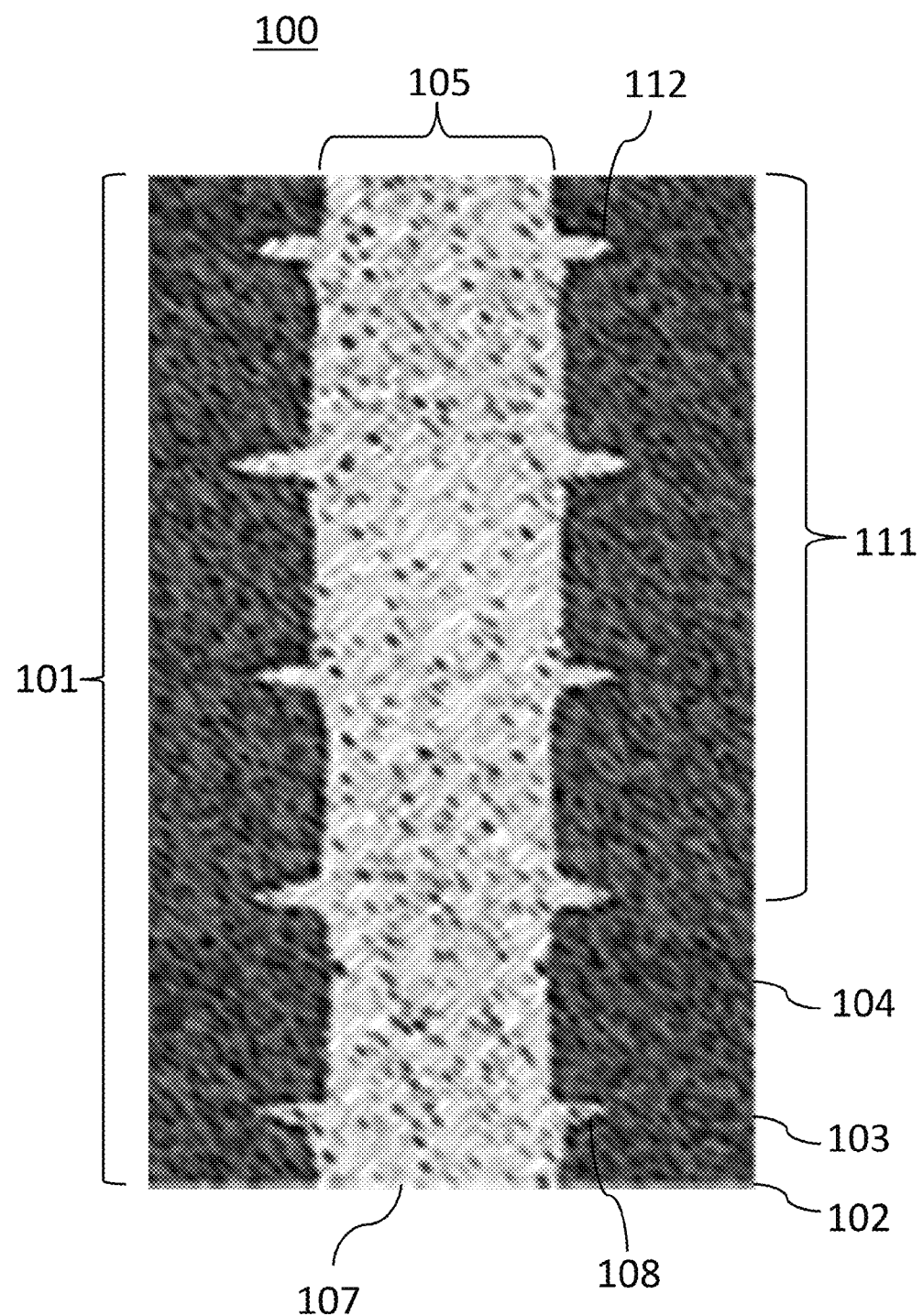
FIG. 7 is a scanning electron microscopy record illustrating a cermet feedthrough according to one embodiment in a cross sectional side view.

FIG. 7 illustrates a scanning electron microscopy record illustrating a cermet feedthrough according to one embodiment in a cross sectional side view. For example, the FIG. 7 illustrates a part of a composite 100 according to one embodiment. The composite 100 is the composite 100 which is schematically illustrated in FIG. 2.

Figure 8:
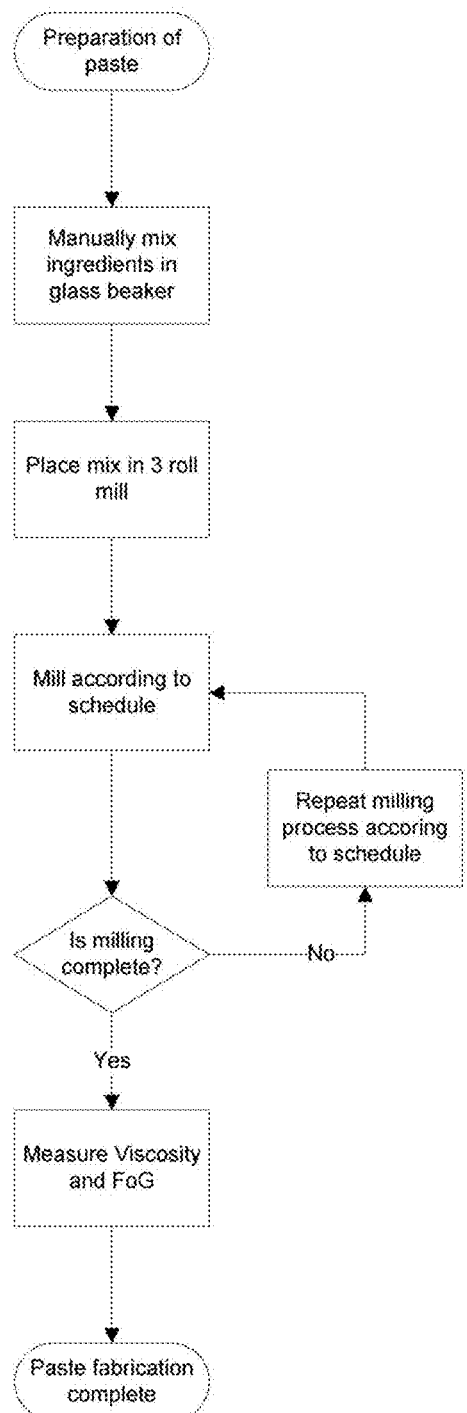
FIG. 8 is a flow chart of an exemplary preparing of a cermet precursor composition according to one embodiment.

FIG. 8 illustrates a flow chart of an exemplary preparing of a cermet precursor composition according to one embodiment. Herein, the cermet precursor composition is referred to as paste. The paste is prepared by manually mixing its ingredients in a glass beaker. Subsequently, the mixed ingredients are milled in a three roll mill. The mixed ingredients are passed through the three roll mill as many times as sufficient for obtaining a homogenised mix, for example 17 times at different adjustments of the rolls of the three roll mill. Subsequently, the viscosity and the fineness of grind of the milled mix are measured to complete the preparation of the paste.

Figure 9:
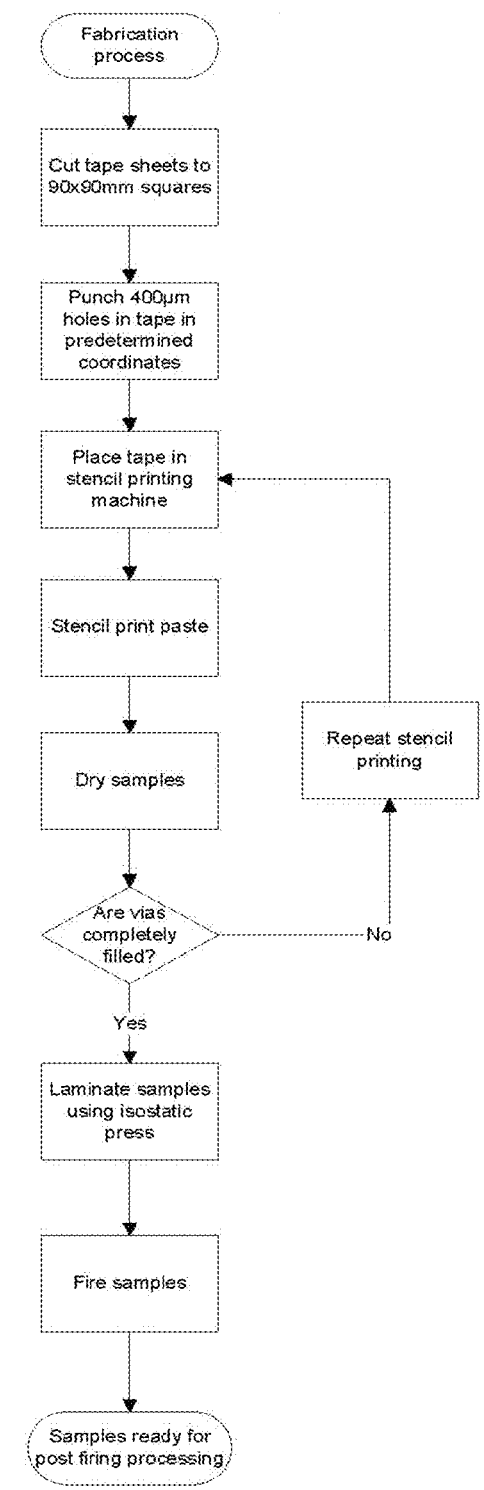
FIG. 9 is a flow chart of an exemplary embodiment of a process according to one embodiment.

FIG. 9 illustrates a flow chart of an exemplary embodiment of a process 900 according to one embodiment. The process 900 is referred to as fabrication process. Green sheet tapes, referred to as tape sheets, are cut to samples squares of dimensions 90 mm×90 mm. Into each tape sheet holes of diameter 400 µm are punched at predetermined coordinates on the tape sheets subsequently. Then each tape sheet is filled with a cermet precursor composition, referred to as paste, subsequently. Said filling is implemented by placing the tape sheet into a stencil printing machine, stencil print the paste into the holes of the tape sheet and drying the tape sheet. The steps of stencil printing paste into the holes and drying the tape sheet are repeated until the holes, in the figure referred to as vias, are completely filled after the last drying step. Subsequently, the tape sheets with completely filled holes are laminated onto each other. The laminate obtained is fired. Subsequently to firing a post firing processing is applied to the laminate.

Figure 10:
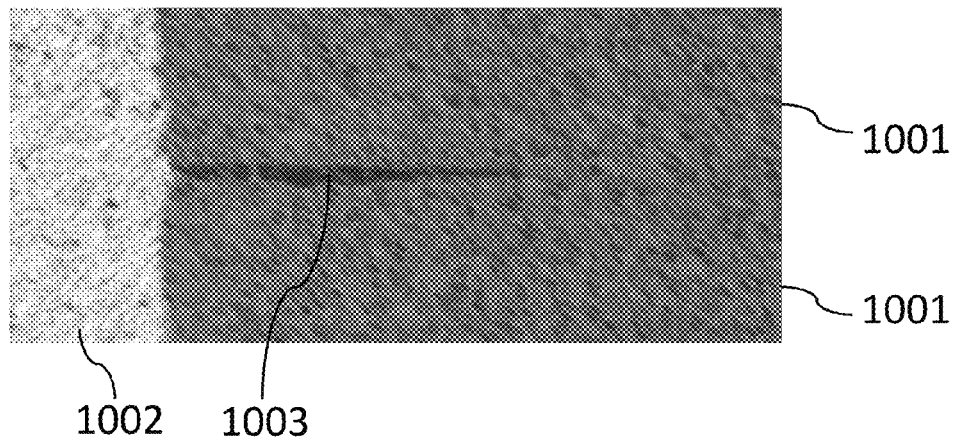
FIG. 10 is a scanning electron microscopy record of a cross section through a composite not according to one embodiment.

FIG. 10 illustrates a scanning electron microscopy record of a cross section through a composite 1000 not according to one embodiment. The figure illustrates two ceramic layers 1001. The ceramic layers 1001 are laminated onto each other. A cermet feedthrough not according to one embodiment 1002 connects through the ceramic layers 1001. At an interface between the ceramic layers 1001 a delamination 1003 is present. This means the lamination of the ceramic layers 1001 is not complete. Such a delamination 1003 can occur upon firing of the ceramic layers 1001 and the cermet feedthrough 1002 due to a stress.

Figure 11:
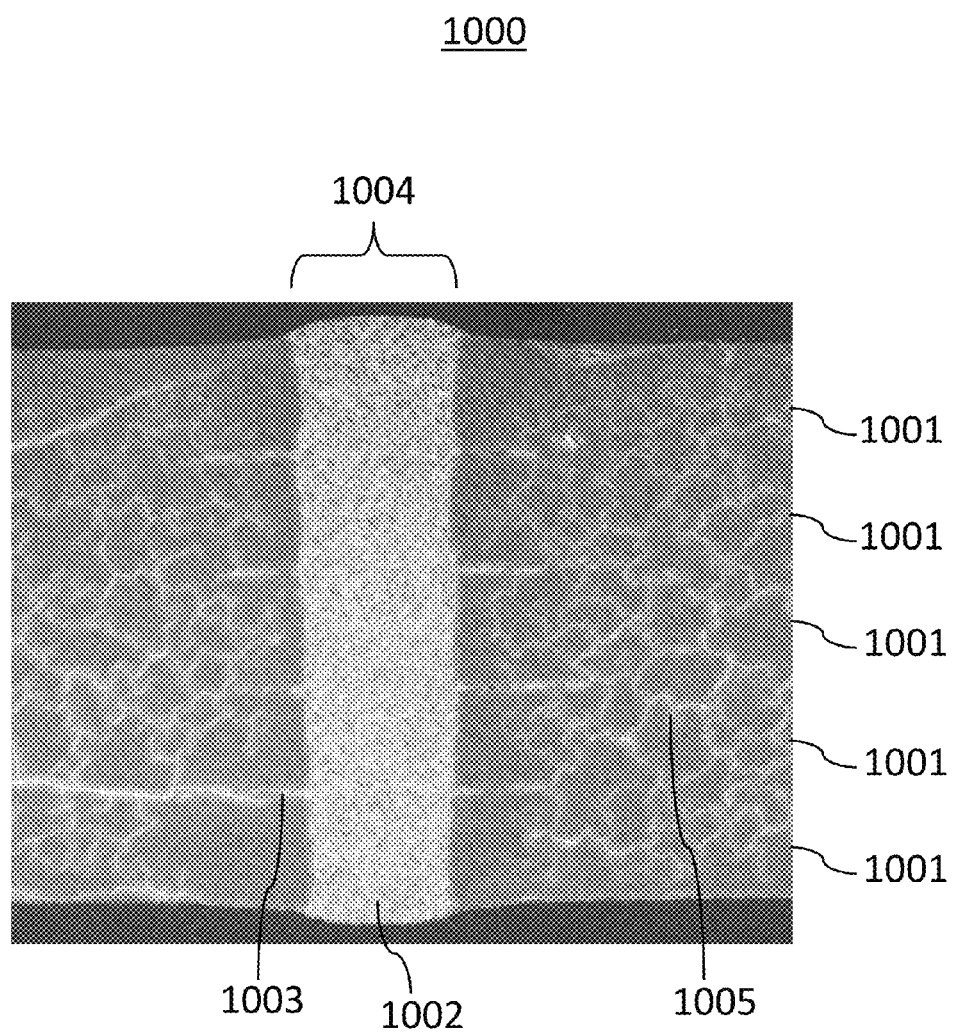
FIG. 11 is a scanning electron microscopy record of a cross section through another composite not according to one embodiment.

FIG. 11 illustrates a scanning electron microscopy record of a cross section through another composite 1000 not according to one embodiment. The composite 1000 includes a plurality of ceramic layers 1001. The ceramic layers 1001 are laminated onto each other. A cermet feedthrough not according to one embodiment 1002 is included by a hole 1004. The cermet feedthrough not according to one embodiment 1002 connects through the plurality of ceramic layers 1001. At an interface between the ceramic layers 1001 a delamination 1003 is present. Furthermore, a structural damage 1005 is present in the ceramic layers 1001.

Figure 12A:
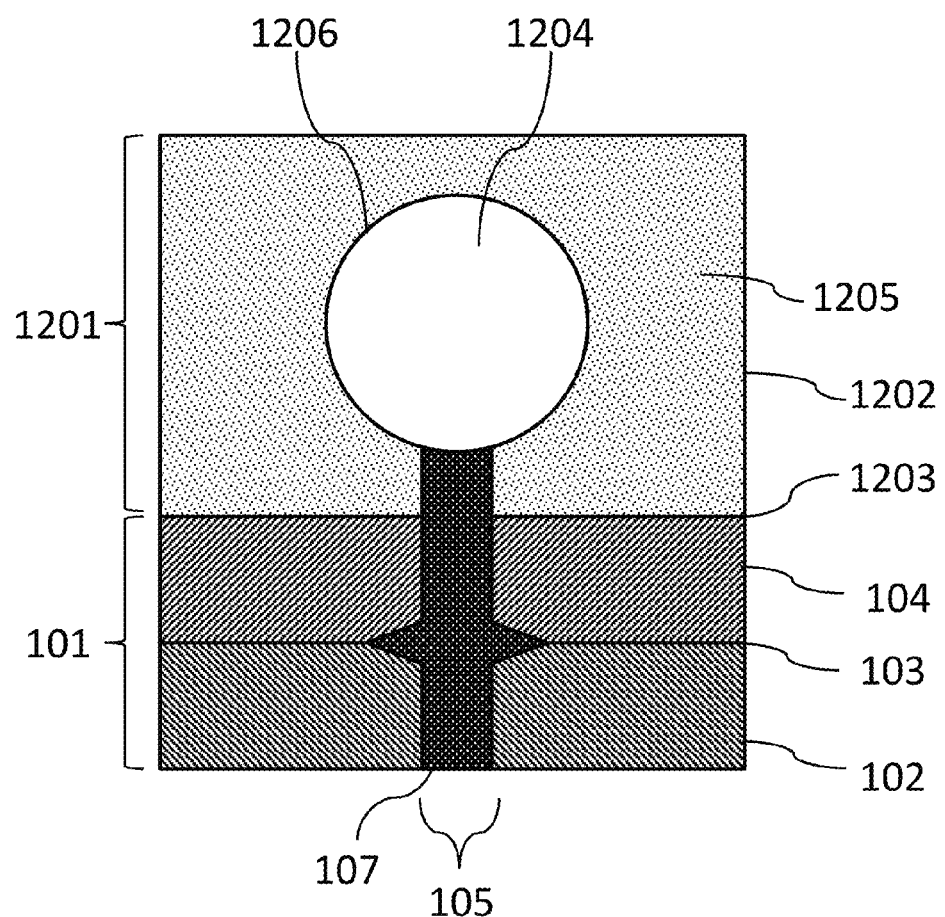
FIG. 12a is a schematic cross sectional side view of another composite according to one embodiment.

FIG. 12a illustrates a schematic cross sectional side view of another composite 100 according to one embodiment. Therein, the composite 100 includes the layer sequence 101 of FIG. 1a. Furthermore, the composite 100 includes a ceramic body 1201, here a ceramic block 1201. The ceramic body 1201 is made of $Al_2O_3$. The ceramic body 1201 includes a ceramic body layer 1202. The ceramic body layer 1202 includes a ceramic body layer surface 1203. The ceramic body layer 1202 superimposes the layer sequence 101 such that the ceramic body layer surface 1203 covers the hole 105. The hole 105 connects through the ceramic body layer surface 1203. The ceramic body 1201 further includes a blind hole. The blind hole includes a blind hole front face 1204 and a blind hole end face 1209. The blind hole front face 1204 is an opening a body surface 1205 of the ceramic body 1201. The blind hole end face 1209 is included by the ceramic body 1201. The body surface 1205 of the ceramic body 1201 is different from the ceramic body layer surface 1203. The blind hole is cylindrical. The blind hole includes a lateral surface 1206. The lateral surface 1206 is a lateral surface of a cylinder. The hole 105 connects through each layer 102, 104 and to the lateral surface 1206 of the blind hole. The first part 107 of the cermet element 106 is included by the hole 105 and connects to the lateral surface 1206 of the blind hole. The blind hole is designed to accommodate a lead. The composite 100 is a header block.

Figure 12B:
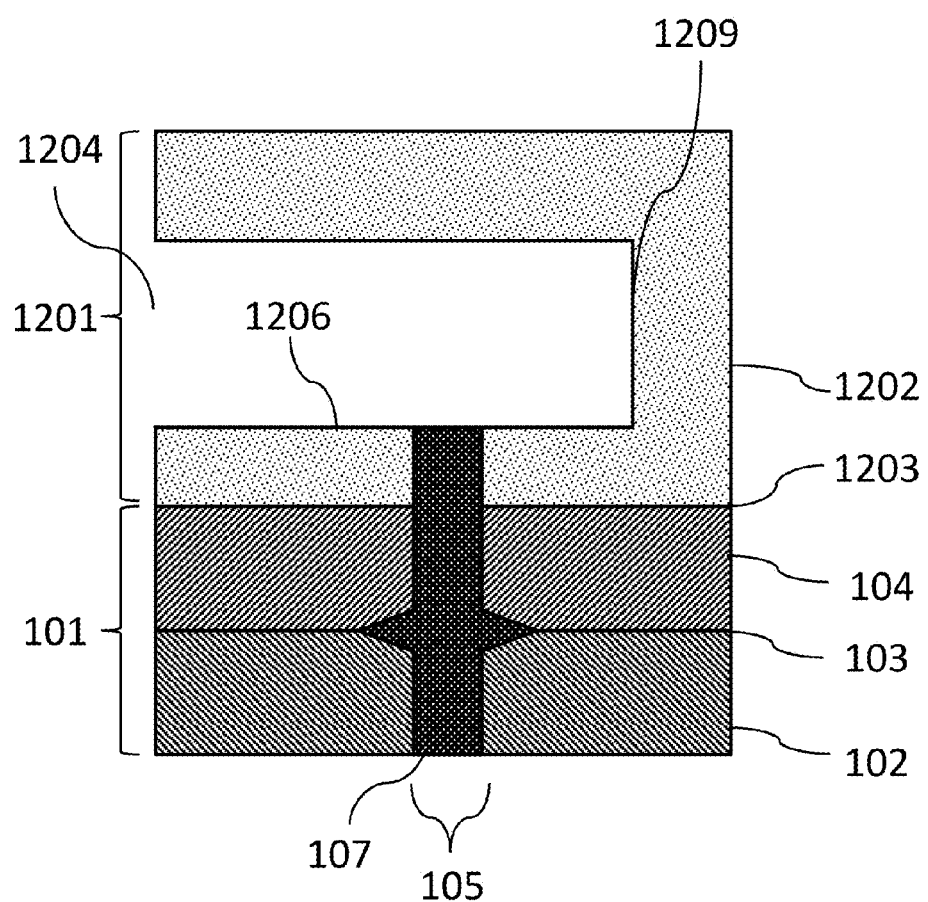

FIG. 12b illustrates another schematic cross sectional side view of the composite 100 according to one embodiment of FIG. 12a. Therein, the side view of FIG. 12b is rotated by 90° with respect to the side view of FIG. 12a.

Figure 13:
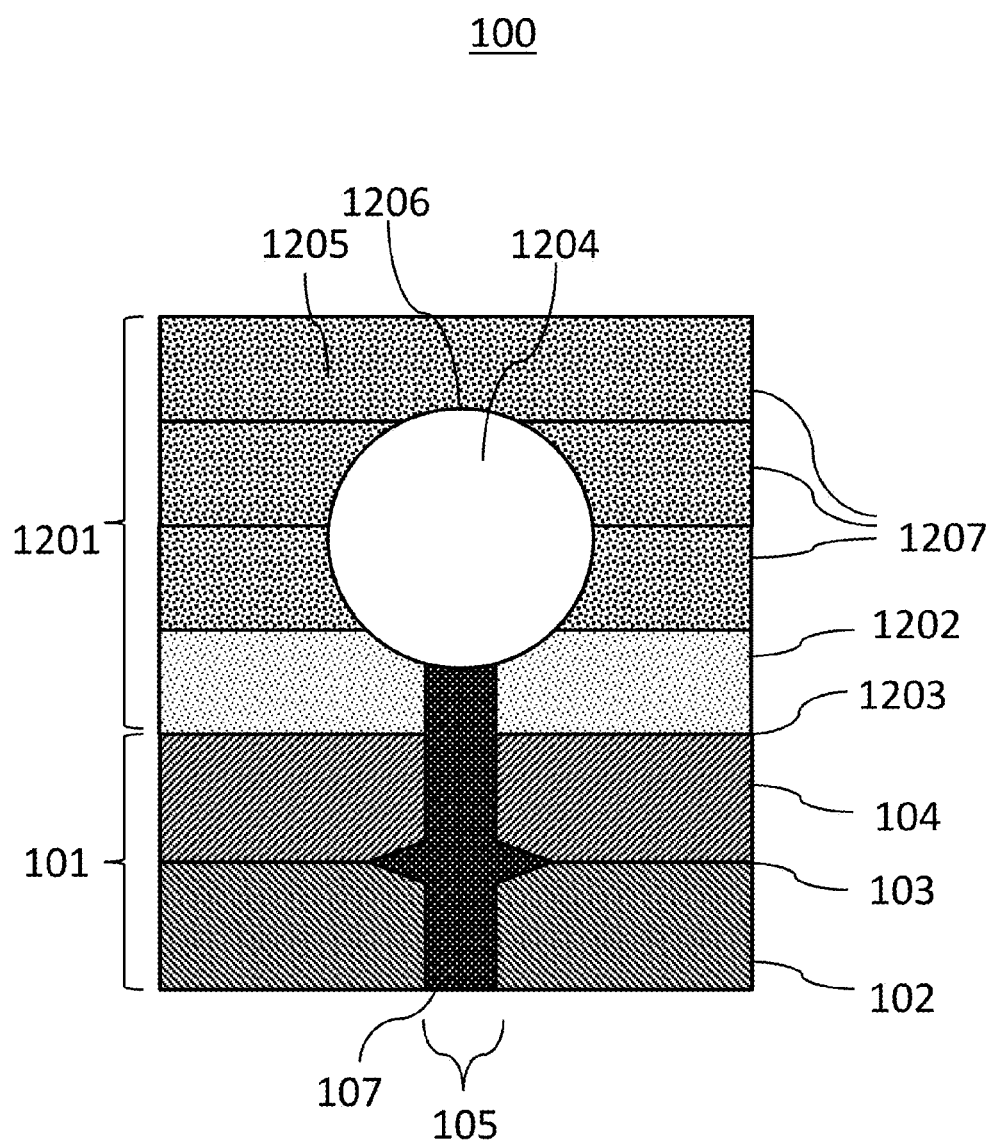
FIG. 13 is a schematic cross sectional side view of another composite according to one embodiment.

FIG. 13 illustrates a schematic cross sectional side view of another composite 100 according to one embodiment. The description of the composite 100 is identical to the description of the composite in FIG. 12a with the exception of the ceramic body 1201 further comprising a plurality of further ceramic body layers 1207.

Figure 14:
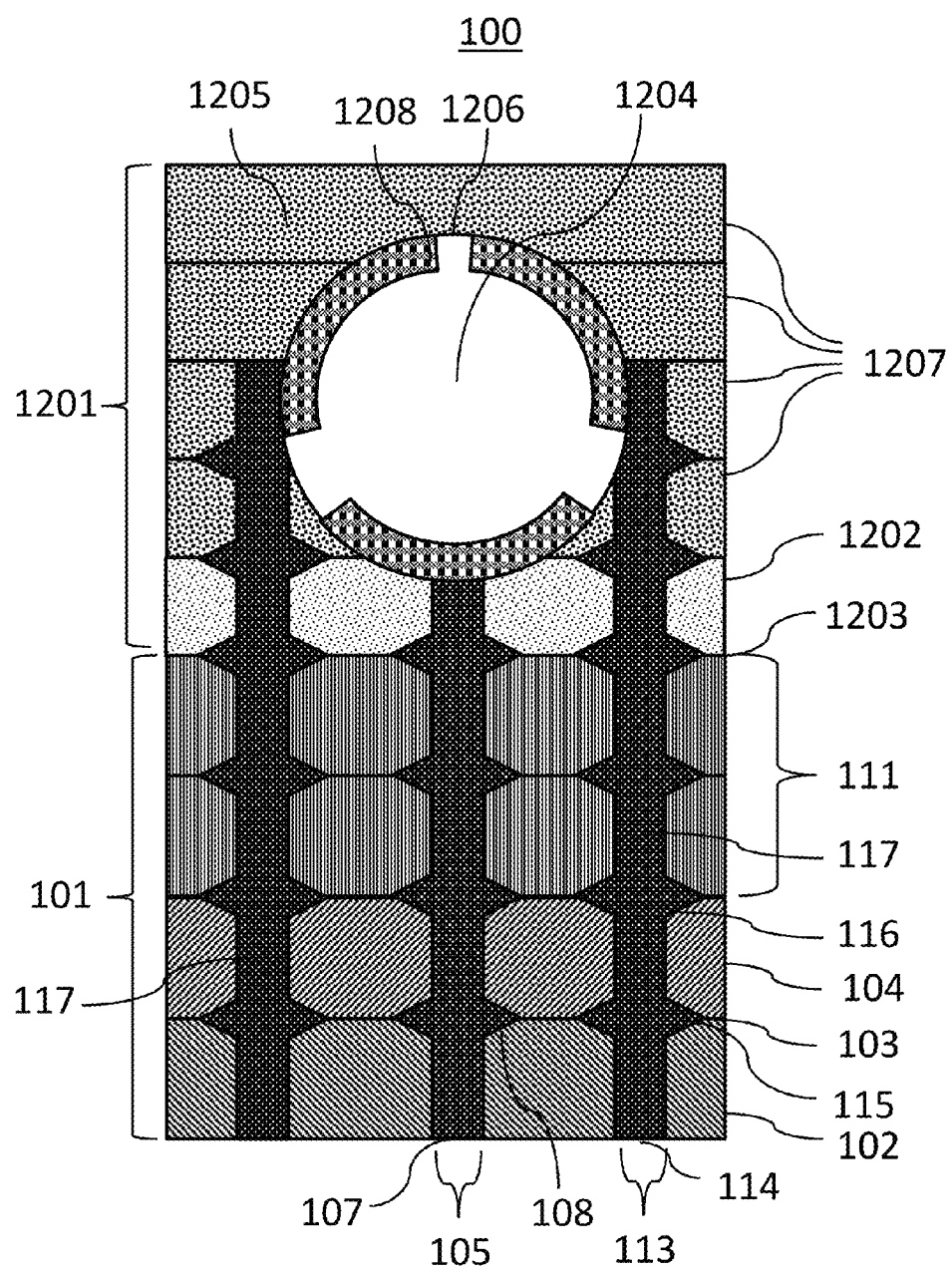
FIG. 14 is a schematic cross sectional side view of another composite according to one embodiment.

FIG. 14 illustrates a schematic cross sectional side view of another composite 100 according to one embodiment. The composite 100 includes a layer sequence 101. The layer sequence 101 includes a first layer 102, comprising a first ceramic and a first layer surface 103, and a second layer 104, comprising a second ceramic. Therein, the second layer 104 superimposes the first layer surface 103. The first ceramic is $Al_2O_3$. The second ceramic is $Al_2O_3$. The layer sequence 101 further includes two layers 111. Each $i^{th}$ layer of the layer sequence 101 includes an $i^{th}$ ceramic. Each $i^{th}$ ceramic is $Al_2O_3$. Each $i^{th}$ layer of the layer sequence 101 further includes an $i^{th}$ layer surface. Therein, each $i^{th}$ layer superimposes the $(i-1)^{th}$ layer. The layer sequence 101 further includes a hole 105, wherein the hole 105 connects through each layer 102, 104, 111 of the layer sequence 101. The hole 105 is about cylindrically shaped. The layer sequence 101 further includes a cermet element 106, which includes four parts 107, 108, 112. Therein, a first part 107 is included by the hole 105. Hence, the first part 107 is about cylindrical. A second part 108 is included between the first layer 102 and the second layer 104. The second part 108 is adjacent to the first layer surface 103. Moreover, the second part 108 is adjacent to the first part 107. Each $i^{th}$ part 108, 112 of the cermet element 106 is included between the $i^{th}$ layer and the $(i-1)^{th}$ layer of the layer sequence 101. Each $i^{th}$ part 108, 112 is adjacent to the first part 107 and the $(i-1)^{th}$ layer surface. Here i can be any integer in the range from 2 to 4. The cermet element 106 is in one piece. The cermet element 106 has a shape similar to a backbone or a bamboo or both. The cermet element 106 includes a cermet, wherein the cermet includes 97 wt.-% Pt and 3 wt.-% $Al_2O_3$, each based on the total weight of the cermet element 106.

In addition, the layer sequence 101 of the composite 100 of FIG. 14 further includes two further holes 113. Each further hole 113 connects through each layer 102, 104, 111 of the layer sequence 101. Each further hole 113 is about cylindrically shaped. Moreover, the layer sequence 101 further includes two further cermet elements 117. Each further cermet element 117 includes four further parts 114, 115, 116. Each further first part 114 is included by one of the further holes 113. Hence, each further first part 114 is about cylindrical. Each further second part 115 is included between the first layer 102 and the second layer 104. Each further second part 115 is adjacent to a further first part 114 and the first layer surface 103. Each further $i^{th}$ part 115, 116 is included between the $i^{th}$ layer and the $(i-1)^{th}$ layer. Each further $i^{th}$ part 115, 116 is adjacent to a further first part 114 and the $(i-1)^{th}$ layer surface. Each further cermet element 117 is in one piece. Here i can be any integer in the range from 2 to 4. Each further cermet element 117 includes a cermet, wherein the cermet includes 97 wt.-% Pt and 3 wt.-% $Al_2O_3$, each based on the total weight of the further cermet element 117. Each further cermet element 117 has a shape similar to a backbone or a bamboo or both.

Additionally, the composite 100 includes a ceramic body 1201, here a ceramic block 1201. The ceramic body 1201 is made of $Al_2O_3$. The ceramic body 1201 includes a ceramic body layer 1202. The ceramic body layer 1202 includes a ceramic body layer surface 1203. The ceramic body layer 1202 superimposes the layer sequence 101 such that the ceramic body layer surface 1203 covers the hole 105 and to the further holes 113. The hole 105 and the further holes 113 each connect through the ceramic body layer surface 1203. The ceramic body 1201 further includes a plurality of further ceramic body layers 1207. Therein, the ceramic layer 1202 and the further ceramic layers 1207 form a further ceramic layer sequence. The ceramic body 1201 further includes a blind hole. The blind hole includes a blind hole front face 1204 and a blind hole end face 1209. The blind hole front face 1204 is an opening a body surface 1205 of the ceramic body 1201. The blind hole end face 1209 is included by the ceramic body 1201. The body surface 1205 of the ceramic body 1201 is different from the ceramic body layer surface 1203. The blind hole is cylindrical. The blind hole includes a lateral surface 1206. The lateral surface 1206 is a lateral surface of a cylinder. The hole 105 connects through each layer 102, 104, 111 of the layer sequence 101 and to the lateral surface 1206 of the blind hole. The first part 107 of the cermet element 106 is included by the hole 105 and connects to the lateral surface 1206 of the blind hole. The cermet element 106 further includes a fifth part. The fifth part is included between the fourth layer of the layer sequence 101 and the ceramic body layer 1202. The fifth part is adjacent to the first part 107 and to the fourth layer surface and the ceramic body layer surface 1203. Each further hole 113 connects through each layer 102, 104, 111 of the layer sequence 101 and to the lateral surface 1206 of the blind hole. Each further first part 114 of each further cermet element 117 is included by a further hole 113 and connects to the lateral surface 1206 of the blind hole. Each further cermet element 117 further includes a further fifth part, a further sixth part and a further seventh part. Each further fifth part is included between the fourth layer of the layer sequence 101 and the ceramic body layer 1202. Each further fifth part is adjacent to a further first part 114 and to the fourth layer surface and the ceramic body layer surface 1203. Each further sixth part is included between the ceramic body layer 1202 and the plurality of further ceramic body layers 1207. Each further seventh part is included between two mutually adjacent further ceramic body layers 1207. Each further seventh part is adjacent to a further first part 114. The blind hole includes a conductive element 1208, here a female connector 1208. The female connector 1208 includes a metal. The female connector 1208 includes 3 parts which are electrically insulated from each other. Each part of the female connector 1208 is electrically connected to a different first part 107 or further first part 114. The first part 107 and the further first parts 114 connect each connect to different positions on the lateral surface 1206. The blind hole is designed to accommodate a lead, wherein the lead electrically connects to the 3 parts of the female connector. The composite 100 is a header block.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A composite, comprising a layer sequence;
   wherein the layer sequence
   a) comprises as layers
      i) a first layer, comprising
         A. a first ceramic, and
         B. a first layer surface,
      ii) a second layer,
         A. comprising a second ceramic,
         B. superimposing the first layer surface;
   b) comprises
      i) a hole, connecting through each layer of the layer sequence;
      ii) a cermet element;
   wherein the cermet element comprises a first part and a second part;
   wherein the first part is comprised by the hole;
   wherein the second part is comprised between the first layer and the second layer;
   wherein the cermet element is in one piece.

2. The composite of claim 1,
   wherein the layer sequence further comprises n layers;
   wherein each $i^{th}$ layer comprises an $i^{th}$ layer surface and an $i^{th}$ ceramic;
   wherein each $i^{th}$ layer superimposes the $(i-1)^{st}$ layer surface;
   wherein the cermet element further comprises n parts;
   wherein each $i^{th}$ part is comprised between the $i^{th}$ layer and the $(i-1)^{st}$ layer;
   wherein n is an integer, being at least 1;
   wherein i is an index which can be any integer selected from the range from 2 to (n+2).

3. The composite of claim 1, wherein the cermet element, or at least one of the further cermet elements, or both comprise:
   a) Pt in the range from 60 weight % to the remainder completing the sum of all components to 100 weight %; and
   b) $Al_2O_3$ in the range from 0.5 to 25 weight %;
   each based on the total weight of the cermet element, or the further cermet element.

4. The composite of claim 1, wherein the second part has a thickness at its widest portion of at least 3 μm.

5. The composite of claim 1, wherein the second part has a length in the range from 5 to 200 μm.

6. The composite of claim 1, wherein the first layer or the second layer or both have a thickness in the range from 75 to 600 μm.

7. The composite of claim 1, wherein the hole has a diameter in the range from 100 to 800 μm.

8. The composite of claim 1, wherein the composite further comprises a ceramic body,
   wherein the ceramic body
   a) comprises a ceramic body layer,
      i) comprising a ceramic body layer surface,
      ii) superimposing the layer sequence such that the ceramic body layer surface covers the hole;
   b) comprises a blind hole, comprising a blind hole front face, a blind hole end face, and a lateral surface;
   wherein the blind hole front face is an opening in a body surface of the ceramic body;
   wherein the body surface is different from the ceramic body layer surface;
   wherein the blind hole end face is comprised by the ceramic body;

wherein the hole connects to the lateral surface;
wherein the first part of the cermet element connects to the lateral surface.

9. A device comprising a hollow body, an inner volume, an outer volume, and the composite of claim 1;
   wherein the hollow body
   a) encloses the inner volume,
   b) separates the inner volume from the outer volume,
   c) comprises an aperture;
   wherein the aperture comprises the composite;
   wherein the composite electrically connects the inner volume to the outer volume.

10. A device comprising a hollow body, an inner volume, an outer volume, and the composite of claim 1;
    wherein the hollow body
    a) encloses the inner volume,
    b) separates the inner volume from the outer volume,
    c) comprises an aperture;
    wherein the aperture frames the composite;
    wherein the blind hole end face is comprised by the inner volume.

11. A use of a plurality of ceramic green sheets and a composition to produce the composite of claim 1;
    wherein the composition comprises
    a) Pt in the range from 60 weight % to the remainder completing the sum of all components to 100 weight %,
    b) $Al_2O_3$ in the range from 0.5 to 25 weight %,
    c) a vehicle in the range from 8 to 30 weight %,
    each based on the total weight of the composition.

12. A method comprising:
    a) providing a first ceramic green sheet, comprising a first hole and a first ceramic green sheet surface, wherein the first hole has a first hole volume;
    b) providing a plurality of portions of a first cermet precursor composition, wherein the plurality of portions of the first cermet precursor composition has a total first cermet precursor composition volume, wherein the total first cermet precursor composition volume is higher than the first hole volume; and
    c) filling the plurality of portions of the first cermet precursor composition into the first hole in subsequent fill-in steps portion by portion, wherein after each fill-in step a filled in portion of the first cermet precursor composition is dried.

13. The method of claim 12, further comprising:
    a) providing a further ceramic green sheet, comprising a further hole and a further ceramic green sheet surface, wherein the further hole has a further hole volume;
    b) providing a further plurality of portions of a further cermet precursor composition, wherein the further plurality of portions of the further cermet precursor composition has a total further cermet precursor composition volume, and wherein the total further cermet precursor composition volume is higher than the further hole volume;
    c) filling the further plurality of portions of the further cermet precursor composition into the further hole in subsequent fill-in steps portion by portion, wherein after each fill-in step a filled in portion of the further cermet precursor composition is dried;
    d) contacting the first ceramic green sheet surface with the further ceramic green sheet surface, wherein the first hole and the further hole are contacted; and
    e) firing the first ceramic green sheet and the further ceramic green sheet.

14. The method of claim 12, wherein the first cermet precursor composition, or the further cermet precursor composition, or both comprises
    a) Pt in the range from 60 weight % to the remainder completing the sum of all components to weight %,
    b) $Al_2O_3$ in the range from 0.5 to 25 weight %,
    c) a vehicle in the range from 8 to 30 weight %,
    each based on the total weight of the first cermet precursor composition or the further cermet precursor composition.

15. The method of claim 12, wherein the contacting of the first ceramic green sheet surface with the further ceramic green sheet surface is a laminating.

16. A composite obtainable by the method of claim 12.

* * * * *